US012350283B2

(12) United States Patent
Estrela Arigüel et al.

(10) Patent No.: US 12,350,283 B2
(45) Date of Patent: Jul. 8, 2025

(54) METHODS AND COMPOSITIONS FOR TREATING MOTOR NEURON DISEASES

(71) Applicants: UNIVERSITAT DE VALENCIA-ESTUDI GENERAL, Valencia (ES); ELYSIUM HEALTH, INC., New York, NY (US)

(72) Inventors: José María Estrela Arigüel, Valencia (ES); Maria Elena Obrador Pla, Valencia (ES); Rosario Salvador, Valencia (ES); Ryan W. Dellinger, Azusa, CA (US)

(73) Assignees: UNIVERSITAT DE VALENCIA-ESTUDI GENERAL, Valencia (ES); ELYSIUM HEALTH, INC., New York, NY (US)

(*) Notice: Subject to any disclaimer, the term of this patent is extended or adjusted under 35 U.S.C. 154(b) by 888 days.

(21) Appl. No.: 17/432,994

(22) PCT Filed: Feb. 25, 2020

(86) PCT No.: PCT/US2020/019600
§ 371 (c)(1),
(2) Date: Aug. 23, 2021

(87) PCT Pub. No.: WO2020/176445
PCT Pub. Date: Sep. 3, 2020

(65) Prior Publication Data

US 2022/0160745 A1 May 26, 2022

Related U.S. Application Data

(60) Provisional application No. 62/892,754, filed on Aug. 28, 2019, provisional application No. 62/810,728, filed on Feb. 26, 2019.

(51) Int. Cl.
*A61K 31/7076* (2006.01)
*A61K 31/05* (2006.01)
*A61K 31/437* (2006.01)

(52) U.S. Cl.
CPC .......... *A61K 31/7076* (2013.01); *A61K 31/05* (2013.01); *A61K 31/437* (2013.01)

(58) Field of Classification Search
CPC .. A61K 31/7076; A61K 31/05; A61K 31/437; A61K 31/573; A61K 31/09; A61K 31/198; A61K 2300/00; A61P 25/28
USPC .......................................................... 514/46
See application file for complete search history.

(56) References Cited

U.S. PATENT DOCUMENTS

| | | | | |
|---|---|---|---|---|
| 9,314,452 | B2 * | 4/2016 | Kalafer .................... | A61K 9/06 |
| 2004/0219552 | A1 | 11/2004 | Ait Ikhlef et al. | |
| 2018/0362570 | A1 * | 12/2018 | Ganapati ................ | A61P 35/00 |

FOREIGN PATENT DOCUMENTS

| | | | |
|---|---|---|---|
| WO | 2018039207 A1 | 3/2018 | |
| WO | 2018/213420 | 11/2018 | |

OTHER PUBLICATIONS

Carrera-Juliá, S., Moreno, M. L., Barrios, C., de la Rubia Ortí, J. E., & Drehmer, E. Antioxidant Alternatives in the Treatment of Amyotrophic Lateral Sclerosis: A Comprehensive Review. Frontiers in Physiology, 11. https://doi.org/10.3389/fphys.2020.00063 (Year: 2020).*

Legg, K. Identifying novel targets of resveratrol. Nature Reviews Drug Discovery, 11(4), 273-273. https://doi.org/10.1038/nrd3717 (Year: 2012).*

Bedlack, R. ALSUntangled 42: Elysium health's "basis." Amyotrophic Lateral Sclerosis and Frontotemporal Degeneration, 19(3-4), 317-319. https://doi.org/10.1080/21678421.2017.1373978 (Year: 2017).*

Glossary of medical education terms, Institute of International Medical Education. http://www.iime.org/glossary.htm. (Year: 2013).*

Oskarsson et al. MN-166 (ibudilast) in amyotrophic lateral sclerosis in a Phase IIb/III study: COMBAT-ALS study design. Neurodegenerative Disease Management, 11(6), 431-443. https://doi.org/10.2217/nmt-2021-0042 (Year: 2021).*

International Search Report issued May 4, 2020 in PCT/US2020/019600.

Andreassen et al., "N-acetyl-L-cysteine improves survival and preserves motor performance in an animal model of familial amyotrophic lateral sclerosis", NeuroReport 11(11): 2491-2493 (2000).

Atencia et al., "Theme 7 In Vivo Experimental Models: P104 Preclinical Trial of a GSK3 and PDE7 Double Inhibitor in SOD1G93A Mice: Gender Specific Effect" Amyotrophic Lateral Sclerosis 12: 113-124 (2011).

Brooks et al., "Adaptive Design Single Center Phosphodiesterase Type 4 (PDE4) Inhibitor—Ibudilast (MN-166-ALS-1201) Phase 1b/ 2a Clinical Trial Double-Blind (DB) with Open Label Extension (OLE) for Amyotrophic Lateral Sclerosis (ALS) Patients [1] Not Requiring Non-Invasive Ventilation (No. NIV) up to 5 years (Early Cohort—EC) and [2] Requiring Non-Invasive Ventilation (NIV) up to 10 years (Advanced NIV Cohort—ANC) from Disease Onset—Report of Clinical Trial DB, OLE and Post-Treatment Cessation of Epochs—Per Protocol (PP) Treatment Completion Associated with Improved Survival and Post Treatment Cessation Loss of Muscle Strength," Neurology 88(16) (2017).

(Continued)

*Primary Examiner* — Yih-Horng Shiao
*Assistant Examiner* — Hoi Yan Lee
(74) *Attorney, Agent, or Firm* — MEDLER FERRO WOODHOUSE & MILLS PLLC

(57) ABSTRACT

Provided herein are methods and compositions related to treating motor neuron diseases, such as ALS, in a subject by administering to the subject (e.g., orally administering to the subject) a composition comprising nicotinamide riboside, pterostilbene and a phosphodiesterase (PDE) inhibitor, including a PDE4 inhibitor such as ibudilast, and also including a thiol/cysteine donor, such as acetylcysteine.

8 Claims, 5 Drawing Sheets

(56) References Cited

OTHER PUBLICATIONS

Cheng et al., "SIRT1 activation by pterostilbene attenuates the skeletal muscle oxidative stress injury and mitochondrial dysfunction induced by ischemia reperfusion injury," Apoptosis 21: 905-916 (2016).

Evans et al., "CNS-targeted glucocorticoid reduces pathology in mouse model of amyotrophic lateral sclerosis," ACTA Neuropathologica Communications 2:66, p. 1-13 (2014).

Frederick et al., "Loss of NAD Homeostasis Leads to Progressive and Reversible Degeneration of Skeletal Muscle," Cell Metabolism 24, 269-282 (2016).

Knott et al., "Phosphodiesterase Inhibitors as a Therapeutic Approach to Neuroprotection and Repair," Int. J. Mol. Sci. 18: 696 (2017).

Liu et al., "Identification of novel N-acetylcysteine derivatives for the treatment of hepatocellular injury," Med. Chem. Comm. 8: 2238 (2017).

Liu and Wang, "Role of Neuroinflammation in Amyotrophic Lateral Sclerosis: Cellular Mechanisms and Therapeutic Implications," Frontiers in Immunology 8: 1005 (2017).

Patel et al., "N-acetylcysteineamide Preserves Mitochondrial Bioenergetics and Improves Functional Recovery Following Spinal Trauma," Exp. Neurol. 257: 95-105 (2014).

Ryu et al., "NAD+ repletion improves muscle function in muscular dystrophy and counters global PARylation," Sci. Transl. Med. 19(8): 361 (2016).

Schepers et al., "Targeting Phosphodiesterases—Towards a Tailor-Made Approach in Multiple Sclerosis Treatment," Frontiers in Immunology 10: 1727 (2019).

Shijie,H. ,"Research and Development of New Drugs", Journal of International Pharmaceutical Research, 44(1): 81 (2017).

Souness et al., "Possible role of cyclic AMP phosphodiesterases in the actions of Ibudilast on eosinophil thromboxane generation and airways smooth muscle tone," Br. J. Pharmacol. 111: 1081-1088 (1994).

Takuma et al., "Ibudilast attenuates astrocyte apoptosis via cyclic GMP signalling pathway in an in vitro reperfusion model," British Journal of Pharmacology 133: 841-848 (2001).

* cited by examiner

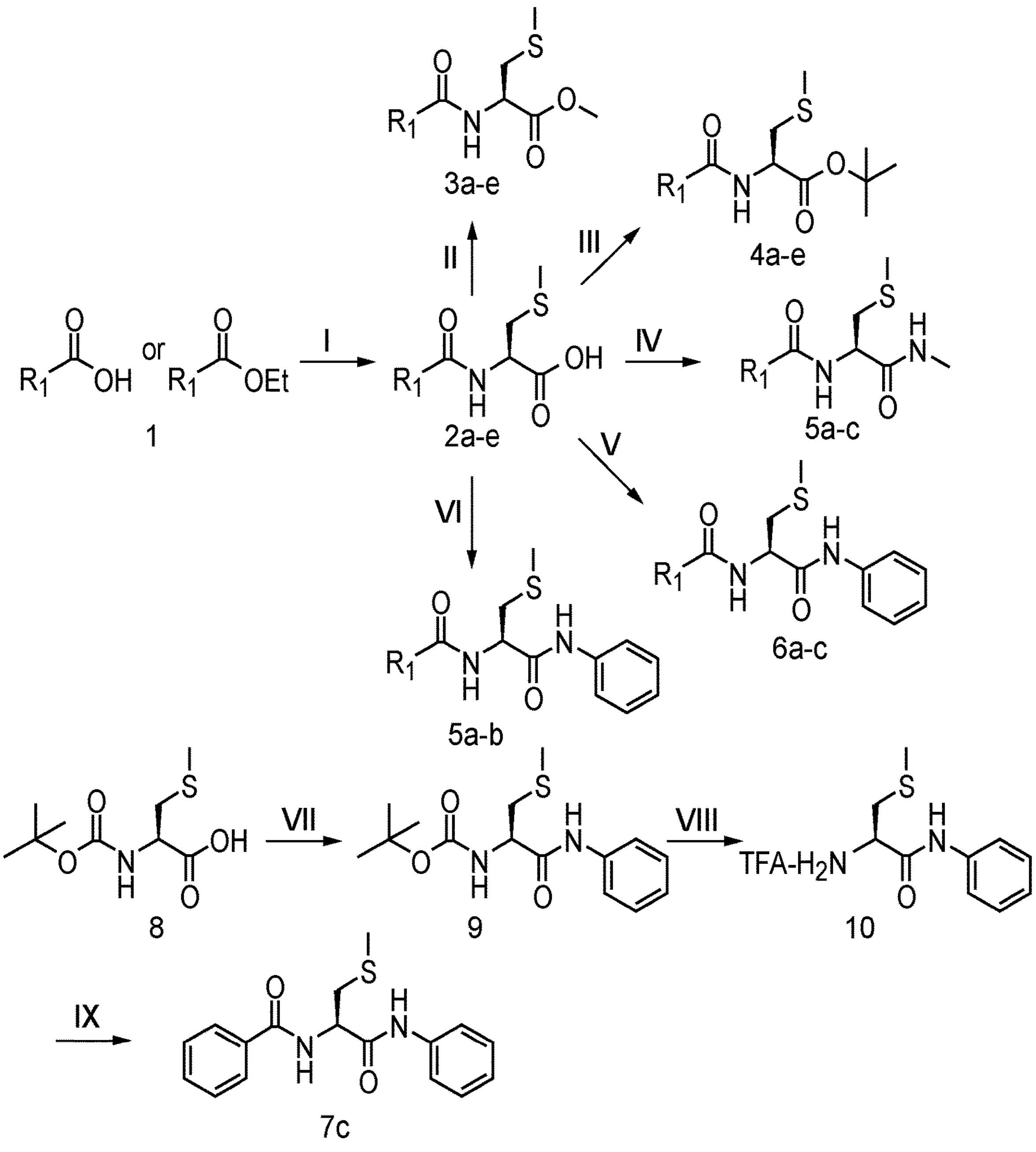

1, 2a-e, 3a-e, 4a-e, 5a-c, 6a-c, 5a-b, 8, 9, 10, 7c 2a, 3a, 4a, 6a, 7a $R_1$ = methyl 2b, 3b, 4b, 5a, 6b, 7b $R_1$ = ethyl 2c, 3c, 4c, 5b $R_1$ = cycohexyl
2d, 3d, 4d, 5c, 6c, 7c $R_1$ = phenyl 2e, 3e, 4e $R_1$ = 4-fluorophenyl

Scheme 1 Synthesis fo target compounds 2a-e, 3a-e, 4a-e, 5a-c, 6a-c and 7a-c. Reagents and conditions: (I) DIE A. Fmoc-Cys)Me)-OH, NMM, DMF, DCM, rt; (II) HCl, MeOH, 15°C; (III) 2-tert-butyl-1,3-diisopropyl-isourea, DCM, 80°C to rt; (IV) methylamine hydrochloride, EDCI, HOBt, DMF, DIEA, 15°C; (v) NMM, IBCF, THF, 0°C; (VI) aniline, HATU, DMF, 15°C or aniline, EDCI, pyridine, 15°C; (VIII) TFA, DCM,15°C (IX) benzoyl chloride, $NaHCO_3$, THF, $H_2O$, 0°C.

FIG. 4

METHODS AND COMPOSITIONS FOR TREATING MOTOR NEURON DISEASES

TECHNICAL FIELD OF THE INVENTION

Provided herein are methods and compositions related to treating motor neuron diseases, such as ALS, in a subject by administering to the subject (e.g., orally administering to the subject) a composition comprising nicotinamide riboside, pterostilbene and a phosphodiesterase (PDE) inhibitor, including a PDE4 inhibitor such as ibudilast. In additional embodiments, a thiol/cysteine donor, such as acetylcysteine can also be added to the composition and/or administered to the subjects to further enhance the treatment.

BACKGROUND OF THE INVENTION

Recent experiments evaluating motor functions in an amyotrophic lateral sclerosis (ALS) model have shown a positive effect resulting from the administration of the association of nicotinamide riboside (NR) and pterostilbene PT (PCT/US 18/32932). Cheng Y, Di S, Fan C, Cai L, Gao C, Jiang P, Hu W, Ma Z, Jiang S, Dong Y, Li T, Wu G, Lv J, Yang Y. SIRT1 activation by pterostilbene attenuates the skeletal muscle oxidative stress injury and mitochondrial dysfunction induced by ischemia reperfusion injury. Apoptosis. 2016 August; 21(8):905-16 have shown that SIRT1 activation by pterostilbene attenuates the skeletal muscle oxidative stress injury and mitochondrial dysfunction induced by ischemia reperfusion injury. Mendelsohn and Larrick (2014) showed that treatment of moderately old mice (first-phase OXPHOS defects) with nicotinamide adenine dinucleotide ($NAD^+$) precursor nicotinamide mononucleotide (NMN) for 1 week restores oxidative phosphorylation activity and other markers of mitochondrial function in skeletal muscle. Moreover it has been shown that loss of $NAD^+$ homeostasis leads to progressive and reversible degeneration of skeletal muscle (Frederick D W, Loro E, Liu L, Davila A Jr, Chellappa K, Silverman I M, Quinn W J 3rd, Gosai S J, Tichy E D, Davis J G, Mourkioti F, Gregory B D, Dellinger R W, Redpath P, Migaud M E, Nakamaru-Ogiso E, Rabinowitz J D, Khurana T S, Baur J A. Loss of NAD Homeostasis Leads to Progressive and Reversible Degeneration of Skeletal Muscle. Cell Metab. 2016 Aug. 9; 24(2): 269-82), and that replenishment of $NAD^+$ may benefit patients with muscular dystrophies or other neuromuscular degenerative conditions characterized by the PARP/NNMT gene expression signatures (Ryu D, Zhang H, Ropelle E R, Sorrentino V, Mázala D A, Mouchiroud L, Marshall P L, Campbell M D, Ali A S, Knowels G M, Bellemin S, Iyer S R, Wang X, Gariani K, Sauve A A, Cantó C, Conley K E, Walter L, Lovering R M, Chin E R, Jasmin B J, Marcinek D J, Menzies K J, Auwerx J. NAD+ repletion improves muscle function in muscular dystrophy and counters global PARylation. Sci Transl Med. 2016 Oct. 19; 8(361): 361ra139). ALS-associated motor neuron degeneration involves damage of the axon, activation of glial cells, and the presence of inflammatory cells. Accumulating evidence suggests that neuroinflammation contributes to neurodegeneration (Ransohoff R M. How neuroinflammation contributes to neurodegeneration. Science 2016; 353: 777-783), a hallmark of ALS. Neuroinflammation is characterized by the presence of reactive astrocytes and microglia, moderate infiltration of peripheral immune cells, and elevated levels of inflammatory mediators, and it has been consistently observed in motor regions of the CNS in sporadic ALS and familiar ALS, constituting a hallmark of the disease (Liu J, Wang F. Role of Neuroinflammation in Amyotrophic Lateral Sclerosis: Cellular Mechanisms and Therapeutic Implications. Front Immunol. 2017 Aug. 21; 8:1005).

A number of clinical trials have tested the effect of various anti-inflammatory drugs in ALS (e.g. glucocorticoids or cyclooxygenase 2 inhibitors) (clinicaltrials.gov). However although there has been a lot of controversy among professional and patients regarding the use of glucocorticoids as an anti-ALS therapy (see e.g. different ALS-related Forums as als.net/forum/yaf_postst49865_dexamethasone.aspx), none of these trials found a therapeutic benefit that would justify its translation into clinical practice. Nevertheless, some interesting observations suggest a potential positive effect. For instance, it has been shown that CNS-targeted anti-inflammatory agent 2B3-201 (liposomal methylprednisolone) has therapeutic potential, reducing brainstem pathology in the SOD1G93A, a mouse model of ALS (Evans M C, Gaillard P J, de Boer M, Appeldoorn C, Dorland R, Sibson N R, Turner M R, Anthony D C, Stolp H B. CNS-targeted glucocorticoid reduces pathology in mouse model of amyotrophic lateral sclerosis. Acta Neuropathol Commun. 2014 Jun. 13; 2:66); or treatment with penicillin G and hydrocortisone reduces ALS-associated symptoms (a case series of three patients) (Tuk B, Jousma H, Gaillard P J. Treatment with penicillin G and hydrocortisone reduces ALS-associated symptoms: a case series of three patients). Comparative oral glucocorticoid potencies indicate that dexamethasone shows the highest potency (Chrousos G, Pavlaki A N, Magiakou M A (2011). "Glucocorticoid Therapy and Adrenal Suppression". PMID 25905379).

Ibudilast (development codes: AV-411 or MN-166) is an anti-inflammatory drug used mainly in Japan, which acts as a phosphodiesterase inhibitor, inhibiting the PDE4 subtype to the greatest extent, but also showing significant inhibition of other PDE subtypes. Ibudilast has bronchodilator, vasodilator and neuroprotective effects, and is mainly used in the treatment of asthma and stroke. It inhibits platelet aggregation, and may also be useful in the treatment of multiple sclerosis. Interestingly Ibudilast, which shows anti-neuroinflammation properties, has been also proposed for the treatment of ALS (Kalafer et al., 2014, U.S. Pat. No. 9,314,452 B2).

BRIEF DESCRIPTION OF THE INVENTION

According to certain aspects, provided herein are methods and compositions related to treating motor neuron diseases (e.g., amyotrophic lateral sclerosis, or ALS) in a subject by administering to the subject (e.g., orally administering to the subject) a compound of Formula I or Formula II (e.g., nicotinamide riboside), a compound of formula III (e.g., pterostilbene) and a phosphodiesterase (PDE) inhibitor (e.g., ibudilast). In certain embodiments, the motor neuron disease is ALS, hereditary spastic paraplegia (HSP), primary lateral sclerosis (PLS), progressive muscular atrophy (PMA), progressive bulbar palsy (PBP), pseudobulbar palsy, or a spinal muscular atrophy. In additional embodiments, acetylcysteine can be added to the compositions and/or administered to the subjects to enhance the treatment.

In certain aspects, the methods and compositions provided herein relate to the slowing or reversing the progression of motor neuron degeneration in a subject by administering to the subject (e.g., orally administering to the subject) a compound of Formula I or Formula II (e.g., nicotinamide riboside), a compound of formula III (e.g., pterostilbene) and a phosphodiesterase (PDE) inhibitor, including PDE1, PDE2, PDE3, PDE4, PDE5, PDE 7, PDE9, PDE10 and PDE11 inhibitors, and in exemplary embodiments PDE4 inhibitors such as ibudilast). In some embodiments, the subject has a motor neuron disease (e.g., ALS, HSP, PLS, PMA, PBP, pseudobulbar palsy or spinal muscular atrophy). In additional embodiments, acetylcysteine can be added to the compositions and/or administered to the subjects to enhance the treatment.

BRIEF DESCRIPTION OF THE FIGURES

FIG. 4 shows the synthesis of derivatives of NAC.

DESCRIPTION OF THE INVENTION

Definitions

Figure 1:
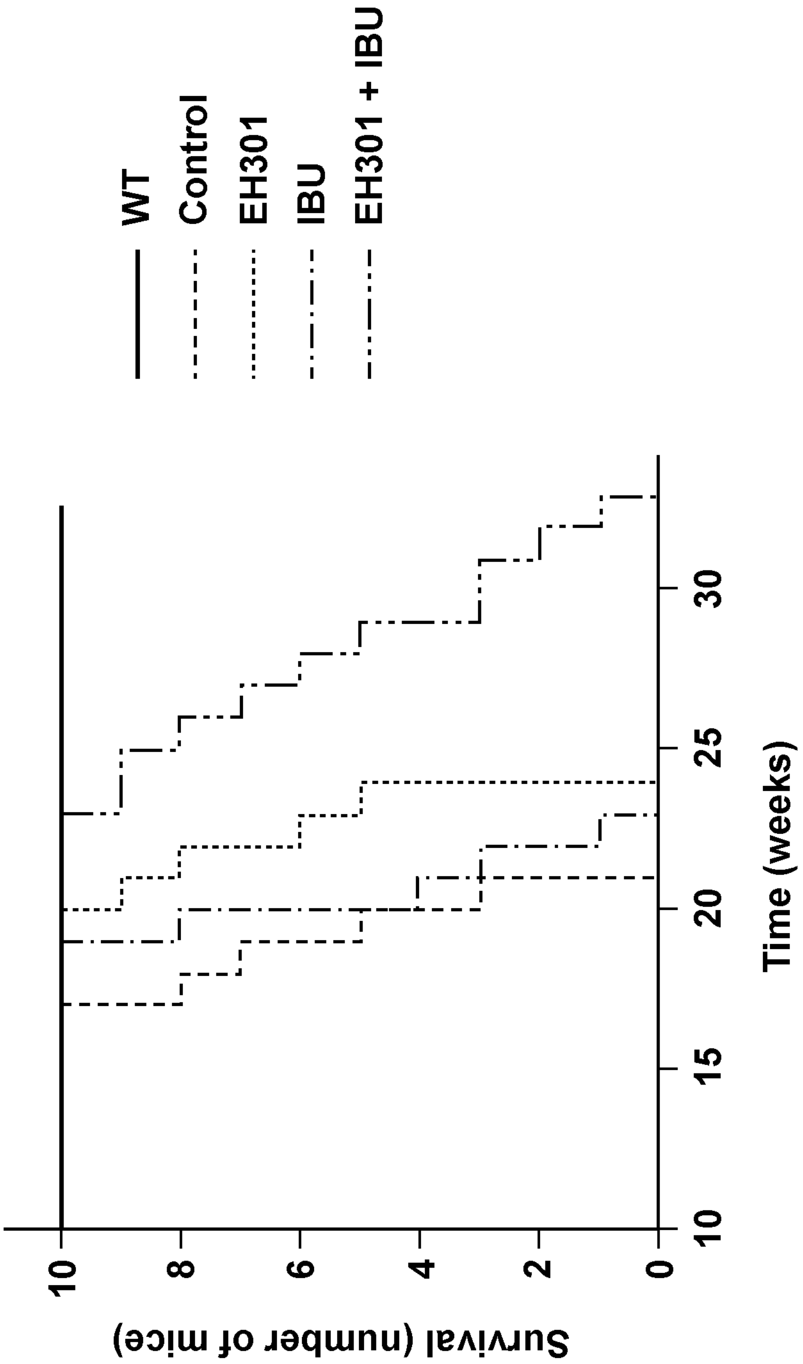
FIG. 1 illustrates a survival assay of SOD1 G93A mice treated with different compositions. WT, wild type. EH301 [Nicotinamide riboside (NR) and pterostilbene (PT)] was administered orally: 185 mg of nicotinamide riboside and/or 30 mg of pterostilbene/Kg×day. Ibudilast (IBU) was administered orally: 12 mg/Kg×day. In this figure it is shown that the combination EH301 and Ibudilast increases survival in the SOD1$^{G93A}$ ALS mouse.

Before describing the present invention in detail, it is to be understood that this invention is not limited to particular administration modes, patient populations, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present invention, the following terminology will be used in accordance with the definitions described below.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecules" or "active agents" as described herein includes at least pterostilbene, nicotinamide riboside and phosphodiesterase (PDE) inhibitors, including ibudilast.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

"Glial cells" refer to various cells of the CNS also known as microglia, astrocytes, and oligodendrocytes.

The terms "subject", "individual" or "patient" are used interchangeably herein and refer to a vertebrate, preferably a mammal. Mammals include, but are not limited to, murines, rodents, simians, humans, farm animals, sport animals and pets. The terms "pharmacologically effective amount" or "therapeutically effective amount" of a composition or agent, as provided herein, refer to a nontoxic but sufficient amount of the composition or agent to provide the desired response, such as a reduction or reversal of ALS. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about", particularly in reference to a given quantity, is meant to encompass deviations of plus or minus five percent.

"Treatment" or "treating" progressive neurodegenerative diseases includes arresting the development or reversing the symptom of a progressive neurodegenerative disease.

The methods of the invention for the treatment of progressive neurodegenerative diseases are based upon administration of the following molecules: pterostilbene, nicotinamide riboside and a phosphodiesterase (PDE) inhibitor, such as ibudilast. "Phosphodiesterase (PDE) inhibitor" refers to a class of compounds that catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: Ca2+/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). PDE inhibitors can also be divided into three broad groups based on their catalytic selectivity to cyclic nucleotides: cyclic AMP-specific PDEs (PDE4, PDE7, and PDE8), cyclic GMP-specific PDEs (PDE5, PDE6, and PDE9), and PDEs that lack specificity, hydrolyzing both cyclic nucleotides (PDE1, PDE2, PDE3, PDE10, and PDE11).

In embodiments, the PDE inhibitors useful in the methods and compositions described herein are PDE1, PDE2, PDE3, PDE4, PDE5, PDE 7, PDE9, PDE10 or PDE11 inhibitors. PDE4 inhibitors are compounds that block the degradative action of phosphodiesterase 4 on cyclic adenosine monophosphate (cAMP). PDE4s act as the main negative regulator of cellular cyclic AMP in the central nervous system, their key activity in maintaining cyclic AMP signal compartmentalization and are implicated in a wide range of neurological diseases and injury.

Ibudilast is a small molecule drug (molecular weight of 230.3) having the structure shown below.

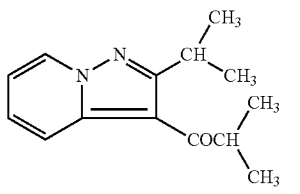

Ibudilast is also found under ChemBank ID 3227, CAS #50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is a is a selective inhibitor of cyclic nucleotide phosphodiesterases (PDEs) 3A, 4, 10A1 and 11A1 (Gibson et al., Eur J Pharmacol 538: 39-42, 2006), and has also been reported to have leukotriene D4 and PAF antagonistic activities. Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247: Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF.alpha. production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848.

Additional PDE inhibitors that can be utilized in the methods described herein include, but are not limited to:

the PDE1 inhibitors Vinpocetine, IC224, IC86340, IC295, Dioclein, Nicardipine, Phenethiazines, Calimidazolium, SCH51866, Nimodipine, and Amantadine;

the PDE 2 inhibitors Luteolin, Exisulind, Oxindole, IC933, BAY60-7550, and EHNA;

the PDE3 inhibitors Cilostazol, Milrinone, Cilostamide, Pimobendan, IBMX, Tresquinsin, Zardaverine, Siguazodan, Enoximone, and PQ-10;

the PDE4 inhibitors Apremilast, Cilomilast, Crisaborole, Diazepam, Luteolin, Mesembrenone, Piclamilast, Roflumilast, Rolipram, Pentoxifylline, Etazolate, olafentrine, Oglemilast, GSK256066, IBMX, Mesembrine, AWD12-281, SCH351591, V-11294A, HT0712, Denbufylline, RO 20-1724, BPN14770, IC486051, Etazolate, GEBR-7b, GSK356278, MK-0952, and L-454560;

the PDE5 inhibitors mirodenafil, dildenafil, tadalafil, vardenafil and avanafil, Sildenafil, Sildenafil citrate, Tadalafil, Icarlin, Udenafil, DA-8159, SK&F 96231, Zaprinast, and Cilomilast;

the PDE7 inhibitors include quinazoline, BRL 50481, Dipyridamole, Thiadiazole, ASB16165, S14 and VP1.15;

the PDE9 inhibitors SCH81566, Zaprinast, BAY 73-6691, and PF-04447943, the PDE10 inhibitors TAK-063, Zaprinast, Dipyridamole, Papaverine, PQ-10, TP-10, and PF-02545920;

the PDE11 inhibitors Tadalafil, BC 11-38, Zaprinast and Dipyridamole.

A discussion of a number of these PDE inhibitors and their use in the treatment of neurodegenerative disorders is provided in Umar and Hoda, "Selective inhibitors of phosphodiesterases: therapeutic promise for neurodegenerative disorders," *Med. Chem. Commun.* 6:2063-2080 (2015); and in Knott et al., "Phosphodiesterase Inhibitors as a Therapeutic Approach to Neuroprotection and Repair," *International Journal of Molecular Sciences* 18:696 (2017) (the disclosures of each of which are incorporated by reference herein in their entireties, particularly for the disclosures of exemplary PDE inhibitors for use in treatment of neurodegenerative disorders).

Nicotinamide riboside is a pyridine-nucleoside form of niacin (i.e., vitamin $B_3$) that serves as a precursor to nicotinamide adenine dinucleotide ($NAD^+$). As used herein, "nicotinamide riboside" also includes nicotinamide riboside salts, such as nicotinamide riboside chloride. The chemical structure of nicotinamide riboside is provided below:

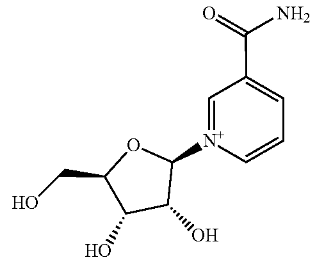 [SMILES: NC(=O)c1ccc[n+]([C@@H]2O[C@H](CO)[C@@H](O)[C@H]2O)c1]

Pterostilbene is a stilbenoid and an analog of polyphenol reservatrol that has better bioavailability due to the presence of two methoxy groups that allow it to have increased lipophilic and oral absorption as well as a longer half-life due to reduced oxidation. The chemical structure of pterostilbene is provided below:

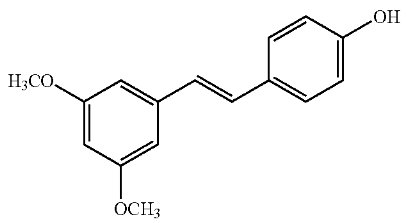 [SMILES: COc1cc(/C=C/c2ccc(O)cc2)cc(OC)c1]

As stated previously, a reference to any one or more of the herein-described drugs, in particular pterostilbene, nicotinamide riboside and ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, and different physical forms.

In additional embodiments, a thiol/cysteine donor, such as acetylcysteine can be added to the compositions and/or administered to the subjects to enhance the treatment.

DESCRIPTION OF THE INVENTION

Figure 2B:
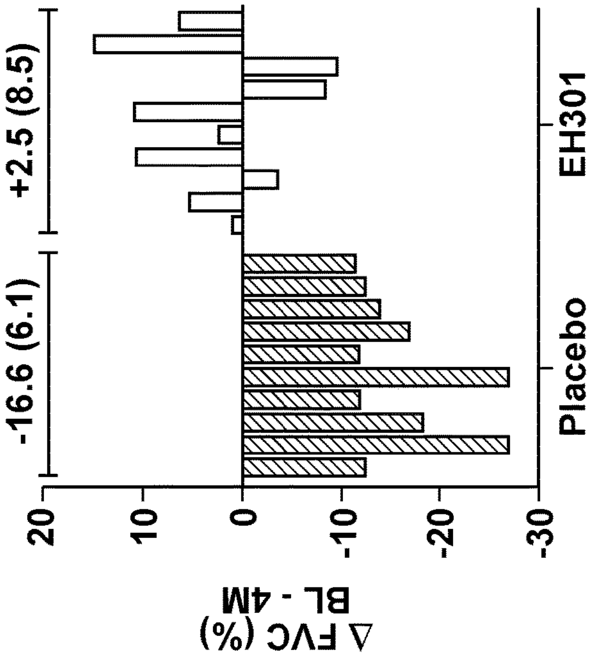
FIGS. 2A-2C illustrate a summary of individual study participant's 4-month change from baseline in (A) ALSFRS-R score, (B) FVC (%) and (C) MRC scale index. All participants enrolled in the trial exhibited a positive response in at least one of the outcome measurements.
Figure 2C:
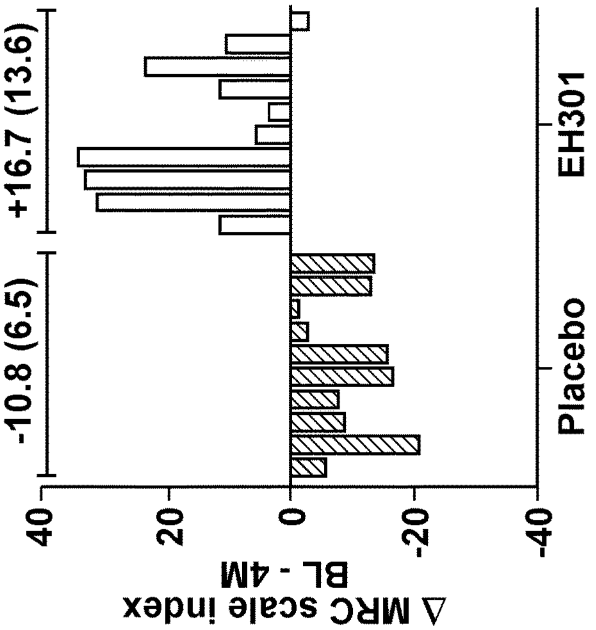
Figure 2A:
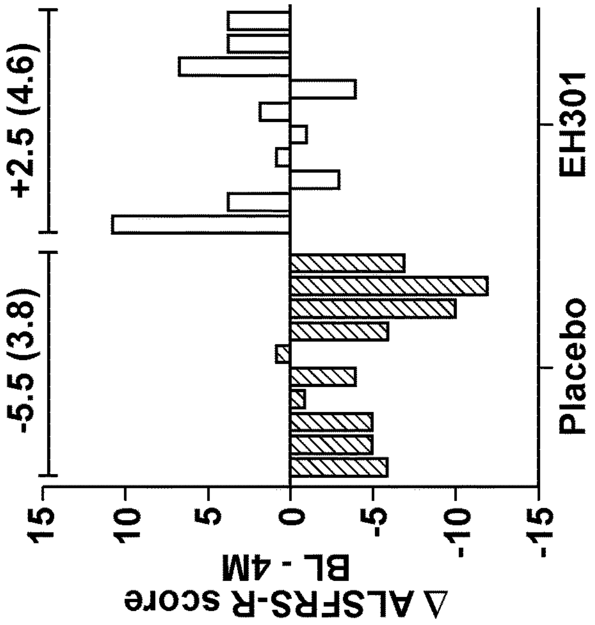

The NAD+ dependent histone deacetylases sirtuins are emerging as therapeutic targets in ALS. Sirtuins regulate cellular processes implicated in ALS, specifically the maintenance of mitochondrial function. Importantly, altered sirtuin levels have been observed in mouse models of ALS and tissues from ALS patients, resulting in deleterious effects on mitochondrial biogenesis, function and turnover. Thus, approaches to sustain sirtuin activity represent promising therapeutic strategies for ALS. Elysium Health have developed EH301, containing two active ingredients—nicotinamide riboside (250 mg) and pterostilbene (50 mg)—which increases NAD+ levels and supports sirtuin activity. EH301 was efficacious in a placebo-controlled, double-blind, human pilot study in people with ALS. Following 4 months of treatment, a striking improvement was observed in all ALS-specific outcome measures in the EH301 treated group compared to placebo at 4 months (FIG. 2), including:

- ALSFRS-R Score: 2.5-point improvement in EH301 group, compared to 5.5-point decline in placebo group (difference between placebo and EH301 at the 4-month time-point=6.1 points)
- FVC: 2.5% improvement in EH301 group, compared to 16.6% decline in placebo group (difference between placebo and EH301 at the 4-month time-point=19.4%)
- MRC Scale Index: 17-point improvement in EH301 group, compared to 11-point decline in placebo group (difference between placebo and EH301 at the 4-month time-point=23 points)

These results were accompanied by significant improvements in muscle activity within the triceps, measured by electromyography. In this trial, all participants were also taking riluzole. No side-effects attributed to the investigational product were observed in any study participants at this dose.

As described herein with reference to the compositions and methods disclosed, the therapeutic benefits of EH301 are further improved with the addition of phosphodiesterase (PDE) inhibitors, including PDE1, PDE2, PDE3, PDE4, PDE5, PDE 7, PDE9, PDE10 and PDE11 inhibitors, and in embodiments PDE4 inhibitors such as Ibudilast. Ibudilast is considered to be a relatively non-specific PDE, although it inhibits the PDE4 subtype to the greatest extent. In fact, a significant improvement in survival was observed in SOD1-G93A mice treated from day 50 with nicotinamide riboside and pterostilbene (EH301) plus Ibudilast (mean survival=191 days), relative to mice treated with either EH301 (mean survival=153 days) or Ibudilast (mean survival=137 days) ($P<0.01$) (see FIG. 1 and table 1). As illustrated in FIG. 1, these findings demonstrate a synergistic interaction between EH301 and Ibudilast, increasing the mean survival by 38 days over EH301 alone and by 54 days over ibudilast alone. These results are surprising and unexpected and represent a unique advantage provided by the present invention over prior therapies for treatment of ALS.

The combination of EH301—containing two active ingredients nicotinamide riboside and pterostilbene—with a PDE inhibitor, including PDE1, PDE2, PDE3, PDE4, PDE5, PDE 7, PDE9, PDE10 and PDE11 inhibitors, and in exemplary embodiments PDE4 inhibitors, represents a unique treatment strategy for ALS, providing improved survival, treatment and/or prevention of motor neuron diseases and disorders (e.g., ALS) and/or for slowing or reversing motor neuron degeneration.

Therefore, provided herein are methods and compositions related to treating and/or preventing motor neuron diseases and disorders (e.g., ALS) and/or for slowing or reversing motor neuron degeneration by administering to a subject in need thereof (e.g., a subject with ALS) a composition comprising a compound of Formula I or Formula II (e.g., nicotinamide riboside), a compound of Formula III (e.g., pterostilbene) and a phosphodiesterase (PDE) inhibitor, including a PDE1, PDE2, PDE3, PDE4, PDE5, PDE 7, PDE9, PDE10 or PDE11 inhibitor, suitably a PDE4 inhibitor such as ibudilast.

Such conjunctive therapy thus includes sequential, simultaneous and separate, or co-administration of the above said compounds of the invention. In embodiments, the therapeutic effects of the first administered compound has not entirely disappeared when the subsequent compounds are administered. That is, the therapeutic effects of the compound of Formula I and/or Formula II (either alone or in combination) have not entirely disappeared when subsequent compounds, including PDE inhibitors, are administered.

As provided herein, pharmaceutical compositions comprising a compound represented by Formula (I) or a pharmaceutically acceptable salt thereof, comprise a compound having the following general chemical structure:

(I)

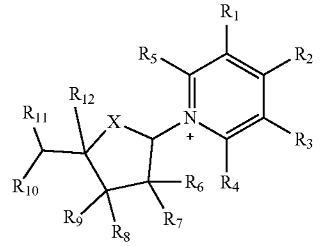

wherein, independently for each occurrence:

- $R_1$, $R_2$, and $R_3$ are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;
- $R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;

$R_6$, $R_8$, $R_{11}$, and $R_{12}$ are selected from hydrogen, ($C_1$-$C_6$) alkyl, —(($C_1$-$C_6$)alkylene)N($R_{14}$)$_m$, —C(O)(($C_1$-$C_6$) alkylene)N($R_{14}$)$_m$, cycloalkyl, heterocycloalkyl, aryl, heteroaryl, aralkyl, heteroaralkyl, —$OR_{14}$, and —N($R_{14}$)$_m$;

$R_7$, $R_9$, and $R_{10}$ are selected from —(($C_1$-$C_6$)alkylene)N ($R_{14}$)$_m$, —$OR_{14}$, and —N($R_{14}$)$_m$;

$R_{13}$ is selected from —$OR_{14}$, —N($R_{14}$)$_m$, —C(O)($R_{14}$), —C(O)($OR_{14}$), —C(O)N($R_{14}$)$_m$, —S(O)$_2$($OR_{14}$), —S(O)$OR_{14}$, and —S(O)$_2$N($R_{14}$)$_m$;

$R_{14}$ is selected from hydrogen, ($C_1$-$C_6$)alkyl, cycloalkyl, heterocycloalkyl, aryl, heteroaryl, aralkyl, and heteroaralkyl; and X is O, S, or N($R_{14}$);

m is 2 or 3;

provided that at least one of $R_1$, $R_2$, and $R_3$ is $R_{13}$.

In some embodiments, $R_1$ is $R_{13}$. In some embodiments, $R_2$ is $R_{13}$. In some embodiments, $R_3$ is $R_{13}$.

In some embodiments, Ru is selected from —$OR_{14}$, —N($R_{14}$)$_m$, —C(O)($R_{14}$), —C(O)($OR_{14}$), and —C(O)N ($R_{14}$)$_m$. In some embodiments, $R_{13}$ is selected from —C(O) ($R_{14}$), —C(O)($OR_{14}$), and —C(O)N($R_{14}$)$_m$. In some embodiments, $R_{13}$ is —C(O)N($R_{14}$)$_m$.

In some embodiments, $R_7$, $R_9$, and $R_{10}$ are each independently —$OR_{14}$ or —N($R_{14}$)$_m$. In some embodiments, $R_7$, $R_9$, and $R_{10}$ are —$OR_{14}$.

In some embodiments, the compound of formula (I) is represented by Formula (II) or a pharmaceutically acceptable salt thereof:

(II)

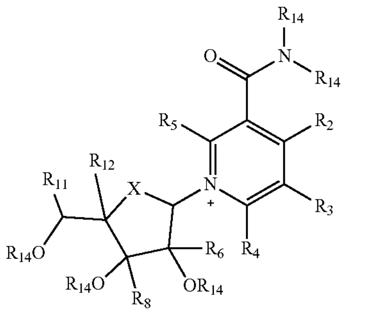

wherein, independently for each occurrence:

$R_2$ and $R_3$ are selected from hydrogen, halogen, —CN, —$NO_2$, —$OR_{14}$, —N($R_{14}$)$_m$, —$R_{13}$, substituted or unsubstituted ($C_1$-$C_6$)alkyl, cycloalkyl, heterocycloalkyl, aryl, heteroaryl, aralkyl, and heteroaralkyl;

$R_4$ and $R_5$ are selected from hydrogen, halogen, —CN, —$NO_2$, —$OR_{14}$, —N($R_{14}$)$_m$, substituted or unsubstituted ($C_1$-$C_6$)alkyl, cycloalkyl, heterocycloalkyl, aryl, heteroaryl, aralkyl, and heteroaralkyl;

$R_6$, $R_8$, $R_{11}$, and $R_{12}$ are selected from hydrogen, —$OR_{14}$, —N($R_{14}$)$_m$, substituted or unsubstituted ($C_1$-$C_6$)alkyl, —(($C_1$-$C_6$)alkylene)N($R_{14}$)$_m$, —C(O)(($C_1$-$C_6$)alkylene)N($R_{14}$)$_m$, cycloalkyl, heterocycloalkyl, aryl, heteroaryl, aralkyl, and heteroaralkyl;

$R_{13}$ is selected from —$OR_{14}$, —N($R_{14}$)$_m$, —C(O)($R_4$), —C(O)($OR_{14}$), —C(O)N($R_{14}$)$_m$, —S(O)$_2$($OR_{14}$), —S(O)$OR_{14}$, and —S(O)$_2$N($R_{14}$)$_m$;

$R_{14}$ is selected from hydrogen, ($C_1$-$C_6$)alkyl, cycloalkyl, heterocycloalkyl, aryl, heteroaryl, aralkyl, and heteroaralkyl; and m is 2 or 3.

In some embodiments of the compounds of formula (I) or (II), $R_1$, $R_2$, and $R_3$ are each independently, if present, selected from hydrogen, halogen, —CN, —$NO_2$, —$OR_{14}$, —N($R_{14}$)$_m$, —$R_{13}$, and substituted or unsubstituted ($C_1$-$C_6$) alkyl. In some embodiments, $R_1$, $R_2$, and $R_3$ are each independently, if present, selected from hydrogen, —$OR_{14}$, —N($R_4$)$_m$, and unsubstituted ($C_1$-$C_6$)alkyl. In some embodiments, $R_1$, $R_2$, and $R_3$ are each independently, if present, selected from substituted or unsubstituted ($C_1$-$C_6$)alkyl, cycloalkyl, heterocycloalkyl, aryl, heteroaryl, aralkyl, and heteroaralkyl. In some embodiments, $R_1$, $R_2$, and $R_3$ are each independently, if present, hydrogen.

In some embodiments of the compounds of formula (I) or (II), $R_4$ and $R_5$ are each independently selected from hydrogen, halogen, —CN, —$NO_2$, —$OR_{14}$, —N($R_{14}$)$_m$, and substituted or unsubstituted ($C_1$-$C_6$)alkyl. In some embodiments, $R_4$ and $R_5$ are each independently selected from hydrogen, —$OR_{14}$, —N($R_{14}$)$_m$, and unsubstituted ($C_1$-$C_6$) alkyl. In some embodiments, $R_4$ and $R_5$ are each independently selected from substituted or unsubstituted ($C_1$-$C_6$) alkyl, cycloalkyl, heterocycloalkyl, aryl, heteroaryl, aralkyl, and heteroaralkyl. In some embodiments, $R_4$ and $R_5$ are each hydrogen.

In some embodiments of the compounds of formula (I) or (II), $R_6$, $R_8$, $R_{11}$, and $R_{12}$ are selected from hydrogen, —$OR_{14}$, —N($R_{14}$)$_m$, unsubstituted ($C_1$-$C_6$)alkyl, —(($C_1$-$C_6$) alkylene)N($R_{14}$)$_m$, —C(O)(($C_1$-$C_6$)alkylene)N($R_{14}$)$_m$, cycloalkyl, heterocycloalkyl, aryl, heteroaryl, aralkyl, and heteroaralkyl. In some embodiments, $R_6$, $R_8$, $R_{11}$, and $R_{12}$ are each independently selected from hydrogen, —$OR_{14}$, —N($R_{14}$)$_m$, unsubstituted ($C_1$-$C_6$)alkyl, —(($C_1$-$C_6$)alkylene)N($R_{14}$)$_m$, and —C(O)(($C_1$-$C_6$)alkylene)N($R_{14}$)$_m$. In some embodiments, $R_6$, $R_8$, $R_{11}$, and $R_{12}$ are each independently selected from hydrogen, —$OR_4$, and —N($R_{14}$)$_m$. In some embodiments, $R_6$, $R_8$, $R_{11}$, and $R_{12}$ are each independently selected from unsubstituted ($C_1$-$C_6$)alkyl, cycloalkyl, heterocycloalkyl, aryl, heteroaryl, aralkyl, and heteroaralkyl. In some embodiments, $R_6$, $R_8$, $R_{11}$, and $R_{12}$ are each hydrogen.

In some embodiments, $R_7$, $R_9$, and $R_{10}$ are each independently —$OR_{14}$ or —N($R_{14}$)$_m$. In some embodiments, $R_7$, $R_9$, and $R_{10}$ are each —$OR_{14}$. In some embodiments, $R_7$, $R_9$, and $R_{10}$ are each —OH.

In some embodiments of the compounds of formula (I) or (II), $R_{14}$ is hydrogen or ($C_1$-$C_6$)alkyl.

In some embodiments of the compounds of formula (I) or (II), X is O or N($R_{14}$). In some embodiments, X is O.

In some embodiments of the compounds of formula (I) or (II), the compound is

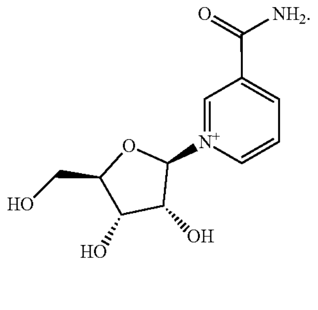 [SMILES: NC(=O)c1ccc[n+]([C@@H]2O[C@H](CO)[C@@H](O)[C@H]2O)c1]

In some embodiments, provided herein are pharmaceutical compositions comprising a compound represented by Formula (III) or a pharmaceutically acceptable salt thereof:

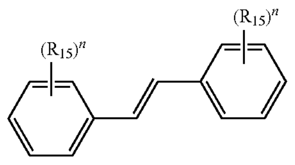
(III)

wherein, independently for each occurrence:

$R_{15}$ is selected from halogen, —CN, —$NO_2$, —$OR_{16}$, —$N(R_{16})_p$, —$S(O)_2(OR_{16})$, —$S(O)OR_{16}$, substituted or unsubstituted ($C_1$-$C_6$)alkyl, cycloalkyl, heterocycloalkyl, aryl, heteroaryl, aralkyl, and heteroaralkyl;

$R_{16}$ is selected from hydrogen, ($C_1$-$C_6$)alkyl, cycloalkyl, heterocycloalkyl, aryl, heteroaryl, aralkyl, and heteroaralkyl;

n is an integer from 0 to 5; and p is 2 or 3;

provided that at least one n is 1; and at least one $R_{15}$ is —$OR_{16}$;

provided that the compound of formula (III) is not

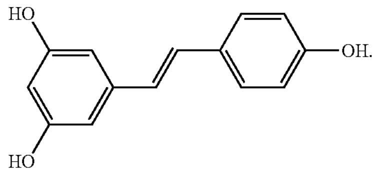 [SMILES: Oc1ccc(/C=C/c2cc(O)cc(O)c2)cc1]

In some embodiments of the compounds of formula (III), $R_{15}$ is selected from, halogen, —CN, —$NO_2$, —$OR_{16}$, —$N(R_{16})_p$, and substituted or unsubstituted ($C_1$-$C_6$)alkyl. In some embodiments, $R_{15}$ is selected from —$OR_{16}$, —$N(R_{16})_p$, and unsubstituted ($C_1$-$C_6$)alkyl. In some embodiments, $R_{15}$ is selected from substituted or unsubstituted ($C_1$-$C_6$)alkyl, cycloalkyl, heterocycloalkyl, aryl, heteroaryl, aralkyl, and heteroaralkyl. In some embodiments, $R_{15}$ is —$OR_{16}$. In some embodiments, $R_5$ is —$OR_{16}$; and $R_{16}$ is hydrogen or ($C_1$-$C_6$)alkyl. In some embodiments, $R_{15}$ is —$OR_{16}$; and $R_{16}$ is ($C_1$-$C_6$)alkyl, cycloalkyl, heterocycloalkyl, aryl, heteroaryl, aralkyl, and heteroaralkyl. In some embodiments, $R_{15}$ is —$OR_{16}$, and $R_{16}$ is ($C_1$-$C_6$)alkyl. In some embodiments, $R_{15}$ is —$OR_{16}$, and $R_{16}$ is ($C_1$-$C_6$)alkyl, cycloalkyl, or heterocycloalkyl.

In some embodiments, n is 1, 2, or 3. In some embodiments, n is 1 or 2.

In some embodiments, p is 2. In some embodiments, p is 3.

It is thus noted that, the present invention refers to pharmaceutically acceptable compositions which comprise a therapeutically-effective amount of a compound of Formula I or Formula II (e.g., nicotinamide riboside), a compound of Formula III (e.g., pterostilbene) and a phosphodiesterase (PDE) inhibitor, such as PDE1, PDE2, PDE3, PDE4, PDE5, PDE 7, PDE9, PDE10, or PDE11 inhibitors, including PDE4 inhibitors such as ibudilast), formulated together with one or more pharmaceutically acceptable carriers (additives) and/or diluents. In another aspect, the present invention refers to a kit of parts wherein said kit comprises pharmaceutically acceptable compositions which comprise a therapeutically-effective amount of a compound of Formula I or Formula II (e.g., nicotinamide riboside) and a compound of Formula III (e.g., pterostilbene), formulated together with one or more pharmaceutically acceptable carriers (additives) and/or diluents, and a further pharmaceutically acceptable composition which comprise a therapeutically-effective amount of a phosphodiesterase (PDE) inhibitor, such as PDE1, PDE2, PDE3, PDE4, PDE5, PDE 7, PDE9, PDE10, or PDE11 inhibitors, including PDE4 inhibitors such as ibudilast with one or more pharmaceutically acceptable carriers (additives) and/or diluents. In another aspect, the present invention refers to a kit of parts wherein said kit comprises a first pharmaceutically acceptable composition which comprises a therapeutically-effective amount of a compound of Formula I or Formula II (e.g., nicotinamide riboside) with one or more pharmaceutically acceptable carriers (additives) and/or diluents; a second pharmaceutically acceptable composition which comprises a therapeutically-effective amount of a compound of Formula III (e.g., pterostilbene) with one or more pharmaceutically acceptable carriers (additives) and/or diluents; and a third pharmaceutically acceptable composition which comprises a therapeutically-effective amount of a phosphodiesterase (PDE) inhibitor, such as PDE1, PDE2, PDE3, PDE4, PDE5, PDE 7, PDE9, PDE10, or PDE11 inhibitors, including PDE4 inhibitors such as ibudilast with one or more pharmaceutically acceptable carriers (additives) and/or diluents.

It is thus noted that the agents described herein, preferably nicotinamide riboside, pterostilbene and the PDE inhibitor such as ibudilast, can be administered as such, or administered in mixtures with pharmaceutically acceptable carriers and can also be administered in conjunction with other agents. Conjunctive therapy thus includes sequential, simultaneous and separate, or co-administration of the above mentioned compounds of the invention. In embodiments, the therapeutic effects of the first administered compound has not entirely disappeared when the subsequent compounds are administered. This includes embodiments when nicotinamide riboside and pterostilbene are administered separately as well as together, and also where a PDE inhibitor is administered together or separately with nicotinamide riboside and pterostilbene.

As described in detail below, the pharmaceutical compositions described herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) sublingually.

In some embodiments, the composition/s comprises additional agents. For example, the composition/s may comprise a nutritional agent, such as an antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In exemplary embodiments, the compositions described herein can further comprise a thiol/cysteine donor. In embodiments, the additional thiol/cysteine donor acetylcysteine can be included. Acetylcysteine, also known as N-Acyty-L-Cysteine (NAC) or N-acetylcysteine, is the amino acid L-cysteine (Cys) along with an acetyl group attached to the amino group, and has the following structure:

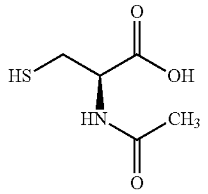

The additional of the acetyl group makes Cys more water-soluble, and functions to speed absorption and distribution on orally ingested Cys. The acetyl group also reduces the reactivity of the thiol (—SH), making NAC less toxic and less susceptible to oxidation than Cys. NAC is safe, even in large doses, and is a better source of Cys than Cys itself. Oral supplementation with NAC has been found to boost intracellular Glutathione (GSH) via elevated intracellular Cys. NAC is rapidly absorbed after oral administration. and reaches a max. plasma level in 2-3 hours, with a half-life of about 6 hours. NAC readily enters cells and is hydrolyzed to cysteine.

The compositions and methods described herein can also include various NAC derivatives and pharmaceutically acceptable salts thereof, including for example NAC amide, NAC ethyl ester, and others. For example, the thiol/cysteine donor can be N-acetylcysteineamide (NACA), for example as disclosed in Patel et al., "N-acetylcysteineamide Preserves Mitochondrial Bioenergetics and Improves Functional Recovery Following Spinal Trauma," *Exp. Neurol.* 257:95-105 (2014), the disclosure of which is incorporated by reference herein in its entirety.

Additional suitable cysteine derivatives that can be utilized in the compositions, formulations and methods described herein are described in Miura et al., "Antioxidant activities of cysteine derivatives against lipid oxidation in anhydrous media," *Bioscience, Biotechnology, and Biochemistry* 78: 1452-1455 (2014), the disclosure of which is incorporated by reference herein, and include the following structures:

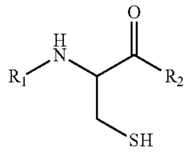

1: $R_1$ = Bz, $R_2$ = $OCH_3$
2: $R_1$ = Bz, $R_2$ = OH
3: $R_1$ = Bz, $R_2$ = $O^-$
4: $R_1$ = Ac, $R_2$ = $OCH_3$
5: $R_1$ = Ac, $R_2$ = OH
6: $R_1$ = Ac, $R_2$ = $O^-$
7: $R_1$ = H, $R_2$ = $OCH_2CH_3$

Further N-acetylcysteine derivatives are disclosed in Liu et al., "Identification of novel N-acetylcysteine derivatives for the treatment of hepatocellular injury," *Med. Chem. Commun.* 8:2238-2247 (2017), the disclosure of which is incorporated by reference herein in its entirety. Liu et al. discloses a number of derivatives of NAC, outlined in the schematic in FIG. 4.

In particular, compounds 6a, 6b, and 7a, can be utilized in the compositions and methods described herein. Compound 6a—(R)-2-Acetamido-N-cyclohexyl-3-(methylthio)propenamide; Compound 6b—(R)—N-Cyclohexyl-3-(methylthio)-2-propionamidopropanamide; and Compound 7a—(R)-2-Acetamido-3-(methylthio)-N-phenylpropanamide. Methods for preparing these compounds are outlined fully in Liu et al.

In still further embodiments, the thiol/cysteine donor can be an N-acetylcysteine benzyl ester or an N-acetylcysteine ethyl ether, for example as disclosed in Uemura et al., "Protective Effects of Brain Infarction by N-Acetylcysteine Derivatives," *Stroke* 49:1727-1733 (2018), the disclosure of which is incorporated by reference herein in its entirety. Synthesis of these NAC derivates is disclosed in Uemura et al. Their structures are illustrated below:

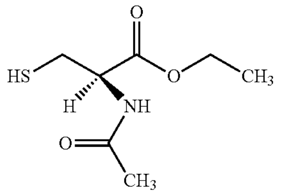

N-Acetylethylcysteine (NACEt)

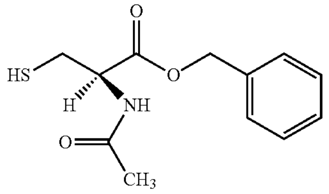

N-Acetylbenzylcysteine (NACBn)

Amounts of the thiol/cysteine donor, suitably acetylcysteine or a derivative thereof that can be included in the compositions described herein can be determined by one of ordinary skill in the art, and will generally range from about 25 mg to about 1000 mg, between about 100 mg and about 1000 mg, between about 25 mg and about 500 mg, between about 25 mg and about 200 mg, between about 25 mg and about 250 mg, between about 30 mg and about 225 mg, between about 40 mg and about 200 mg, between about 45 mg and about 250 mg, or about 25 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg.

Additional compounds that can be included in the compositions and formulations described herein are for example, acamprosate, baclofen, cinacalcet, mexiletine, sulfisoxazole, torasemide and riluzole.

The formulations of the compounds described herein may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation described herein comprises an excipient, including, but not limited to, cyclodextrins, liposomes, micelle forming agents, e.g., bile acids, and polymeric carriers, e.g., polyesters and polyanhydrides; and an agent of the invention. In some embodiments, an aforementioned formulation renders orally bioavailable an agent of the invention. Methods of preparing these formulations or compositions may include the step of bringing into association a compound of the invention with the carrier and, optionally, one or more accessory ingredients.

Liquid dosage forms for oral administration of the formulations provided herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations provided herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary, or paste.

In solid dosage forms of the invention for oral administration (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions described herein may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Pharmaceutical composition/s provided herein suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, coconut oils, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Therapeutic Methods

Provided herein are methods of treating a motor neuron disease or disorder in a subject by administering to the subject (e.g., a subject in need thereof) a therapeutically-effective amount of a compound of Formula I or Formula II (e.g., nicotinamide riboside), a compound of Formula III (e.g., pterostilbene) and a phosphodiesterase (PDE) inhibitor, such as PDE1, PDE2, PDE3, PDE4, PDE5, PDE 7, PDE9, PDE10, or PDE11 inhibitors, including PDE4 inhibitors such as ibudilast. In further embodiments, an additional compound, including for example a thiol/cysteine donor such as acetylcysteine, can also be administered along with the NR, PT and PDE4 inhibitor. Such administration should be thus meant as a conjunctive therapy which includes sequential, simultaneous and separate, or co-administration of the above mentioned compounds of the invention. In embodiments, the therapeutic effects of a first administered compound has not entirely disappeared when the subsequent compounds are administered.

In some aspects, provided herein are methods of slowing or reversing the progression of motor neuron degeneration in a subject comprising administering to the subject (e.g., a subject in need thereof) a therapeutically-effective amount of a compound of Formula I or Formula II (e.g., nicotinamide riboside), a compound of Formula III (e.g., pterostilbene) and a phosphodiesterase (PDE) inhibitor, such as PDE1, PDE2, PDE3, PDE4, PDE5, PDE 7, PDE9, PDE10, or PDE11 inhibitors, including PDE4 inhibitors such as ibudilast. In some embodiments, motor neuron degeneration refers to the death of neurons and/or the loss of neuron function.

In some embodiments, the subject may have or be predisposed to a motor neuron disease (e.g., amyotrophic lateral sclerosis (ALS), such as medulla ALS or brainstem ALS). A motor neuron disease or disorder may be any disease or disorder that affects the function or structure of motor neuron. As used herein, a motor neuron diseases include progressive diseases that result in loss of function of motor neurons, or nerves, in the brain and spinal cord. Examples of motor neuron diseases include amyotrophic lateral sclerosis (ALS), hereditary spastic paraplegia (HSP), primary lateral sclerosis (PLS), progressive muscular atrophy (PMA), progressive bulbar palsy (PBP), pseudobulbar palsy, or a spinal muscular atrophy. A motor neuron disease may affect the upper motor neurons or the lower motor neurons.

Actual dosage levels and administration regimen of the compositions disclosed herein may be varied so as to obtain an amount of a compound of Formula I or Formula II (e.g., nicotinamide riboside), of a compound of Formula III (e.g., pterostilbene) and of a phosphodiesterase (PDE) inhibitor such as PDE1, PDE2, PDE3, PDE4, PDE5, PDE 7, PDE9, PDE10, or PDE11 inhibitors, including PDE4 inhibitors such as ibudilast, that is effective to achieve the desired therapeutic response for a particular patient, composition, and mode of administration, without being toxic to the patient. The dosage of a thiol/cysteine donor such as acetylcysteine that can be administered is also effective to achieve the desired therapeutic response for a particular patient, composition, and mode of administration, without being toxic to the patient, and in general is in the range of about 50-200 mg/kg, suitably about 80-150 mg/kg, or about 100 mg/kg.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, at least 2900 mg, or at least 3000 mg, of a compound of Formula I or Formula II (e.g., nicotinamide riboside). In some embodiments, the dose comprises at least 5 mg, at least 10, at least 20 mg, at least 30 mg, at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg, at least 600 mg, at least 700 mg, at least 800 mg, at least 900 mg, or at least 1000 mg of a compound of formula III (e.g., pterostilbene).

In exemplary embodiments, nicotinamide riboside or its equivalents, alone or in combination with pterostilbene or its equivalents, is administered to a patient (either via a single composition, or in multiple, separate compositions) in an amount of between about 50 mg and about 1500 mg, between about 100 mg and about 1500 mg, between about 100 mg and about 1000 mg, between about 125 mg and about 900 mg, between about 150 mg and about 850 mg, between about 200 mg to 700 mg, between about 200 mg to about 500 mg, between about 1000 mg and about 1500 mg, or about 100 mg, about 150 mg, about 200 mg, about 250 mg, about 300 mg, about 350 mg, about 400 mg, about 450 mg, about 500 mg, about 550 mg, about 600 mg, about 650 mg or about 700 mg. Suitably, these amounts are administered to a patient on a daily basis in the form of a single composition or multiple compositions.

In exemplary embodiments, pterostilbene or its equivalents, alone or in combination with nicotinamide riboside or its equivalents, is administered to a patient (either via a single composition or in multiple, separate compositions) in an amount between about 25 mg and about 1000 mg, between about 100 mg and about 1000 mg, between about 25 mg and about 500 mg per day, between about 25 mg and about 200 mg, between about 25 mg and about 250 mg, between about 30 mg and about 225 mg, between about 40 mg and about 200 mg, between about 45 mg and about 250 mg, or about 25 mg, about 30 mg, about 40 mg, about 50 mg, about 60 mg, about 70 mg, about 80 mg, about 90 mg, about 100 mg, about 110 mg, about 120 mg, about 130 mg, about 140 mg, or about 150 mg. Suitably, these amounts are administered to a patient on a daily basis in the form of a single composition or multiple compositions.

In some embodiments, the dose comprises an amount ranging from about 30 mg to 240 mg, or from about 30 mg to 180 mg, 60 mg to 120 mg, or 20 to 80 mg of a phosphodiesterase (PDE) inhibitor such as PDE1, PDE2, PDE3, PDE4, PDE5, PDE 7, PDE9, PDE10, or PDE11 inhibitors, including PDE4 inhibitors such as ibudilast. For example, the PDE inhibitor, including a PDE1, PDE2, PDE3, PDE4, PDE5, PDE 7, PDE9, PDE10, or PDE11 inhibitor such as those described herein, can be administered at an amount of about 10 mg to 500 mg, about 20 mg to about 400 mg, about 30 mg to about 300 mg, about 40 mg to about 200 mg, about 50 mg to about 100 mg, about 20 mg to about 200 mg, about 20 mg to about 100 mg, about 20 mg to about 50 mg, or about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, including and values and ranges within these ranges.

In some embodiments, the dosage comprises an amount ranging from about 30 mg to 240 mg, or from about 30 mg to 180 mg, 60 mg to 120 mg, or 20 to 80 mg of a thiol/cysteine donor such as acetylcysteine.

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In some embodiments, the subject is given a test to measure the general progression or symptomatic progression of a motor neuron disease. In some embodiments, the subject is given a motor function test and/or a cognition and conduct function test. The motor function test may be Revised Amyotrophic Lateral Sclerosis Functional Rating Scale (ALSFRS-R). The cognition and conduct test may be Complutense Verbal Learning Test (TAVEC), Symbol Digit Modalities Test (SDMT), Verbal Fluency Test, Digit Span (Wechsler Memory Scale III), D2 Attention Test, Wechsler Memory Scale III for Letters and Numbers, London Tower Test, Stroop test, Frontal System Behavior Scale (FrSBe), and/or Brief Test (subjective conduct). In some embodiments, subjects are given both motor function and cognitive function tests. Motor function or cognitive functions tests may be given to the subject once or multiple times.

In some embodiments, the method further comprises measuring a feature (e.g., a feature associated with inflammation) in the subject. In some embodiments, the feature is measured in a blood test. Examples of features that may be tested are the level of a cytokine, level of amyloid A protein, level of macrophage activation marker neopterin, level of creatine phosphokinase (CPK), level of erythrocyte sedimentation rate, level of C-reactive protein, plasma viscosity, and/or white blood cell count. In some embodiments, the cytokine is proinflammatory cytokine. In some embodiments, the cytokine is an anti-inflammatory cytokine. Examples of cytokines include, but are not limited to, TNFα, IFNγ, IL-1, IL-6, IL-8, or TGFβ.

In some embodiments, the method further comprises administering a fatty acid supplement to the subject. In some embodiments, the fatty acid supplement comprises an oil. The oil may be processed (e.g., refined, bleached, or deodorized). In other embodiments, the oil is unprocessed or a virgin oil. In some embodiments, the fatty acid supplement is derived or fractionated from a source to yield separated fatty acids. In some embodiments, the oil is a coconut oil. Coconut oil, as used herein, may include any oil produced by the nut of the coconut palm. Fatty acids found in the supplements disclosed herein may be short-chain fatty acids, medium chain fatty acids, or long chain fatty acids. Exemplary fatty acids that may be found in the supplement include, but are not limited to, caproic acid, caprylic acid, capric acid, lauric acid, myristic acid, palmitic acid, palmitoleic acid, stearic acid, oleic acid, linoleic acid, and/or linolenic acid. The fatty acid supplement disclosed herein may comprise saturated fatty acids, unsaturated fatty acids, monounsaturated fatty acids, and/or polyunsaturated fatty acids. In some embodiments, the fatty acid supplement may comprise a hydrogenated oil. Fatty acid supplements may comprise one or more fatty acid(s). Actual dosage levels and administration regimen of the fatty acid supplement disclosed herein may be varied so as to obtain an amount of fatty acid supplement that is effective to achieve the desired therapeutic response for a particular patient, composition, and mode of administration, without being toxic to the patient.

As described herein, in additional embodiments, the compositions and methods further include the administration of a thiol/cysteine donor such as acetylcysteine. As shown in the Examples, it has been surprisingly found that the addition of a thiol/cysteine donor such as acetylcysteine provides enhanced improvement of the general progression or symptomatic progression of treatment of a motor neuron disease, above that experienced by any of the compounds individually (i.e., nicotinamide riboside, pterostilbene), a phosphodiesterase (PDE) inhibitor, and/or acetylcysteine, alone or in combination. This synergistic finding is a surprising and unexpected advantage of the compositions and methods described herein.

The following examples are merely for illustrative purposes and do not limit the present invention.

EXAMPLES

Glossary of Terms

Pterostilbene (PT); Nicotinamide riboside (NR); EH301 [Nicotinamide riboside (NR) and pterostilbene (PT)]; Dexamethasone (DXM); and Ibudilast (IB).

Objective

The objective of these examples is to investigate if potentially anti-neuroinflammatory drugs such as dexamethasone or ibudilast can further improve or potentiate the effect of nicotinamide riboside (NR) and pterostilbene (PT) in motor functions in mouse models of ALS.

Materials/Methods and Results

Mice

1. B6.Cg-Tg (SOD1*G93A)1Gur/J (jax.org/strain/004435)

Mice hemizygous for SOD1-G93A (also called G93A-SOD1) transgene are viable and fertile, with transgenic expression of a G93A mutant form of human SOD1. This founder line (often referred to as G1H) is reported to have a high transgene copy number. Hemizygotes exhibit a phenotype similar to amyotrophic lateral sclerosis (ALS) in humans; becoming paralyzed in one or more limbs with paralysis due to loss of motor neurons from the spinal cord. Motor neuron degeneration has been associated with function and/or degeneration of astrocytes, the major glial cell type of the nervous system. Transgenic mice have an abbreviated life span: 50% survive at 157.1+/−9.3 days (in contrast to the mixed B6SJL background where 50% survival is observed at 128.9+/−9.1 days). Female hemizygotes are poor breeders, and rarely produce more than one litter before the onset of disease. In contrast to LPS-induced microglia and activated M1/M2 macrophages, spinal cord microglia activated by disease progression do not up-regulate genes that display a bias to either an M1 (neurotoxic) phenotype or an M2 (protective) phenotype. The pattern of gene expression in SOD1G93A activated microglia represents a unique ALS-specific signature. These SOD1-G93A (also called G93A-SOD1) transgenic mice us thus useful in studying neuromuscular disorders, including Amyotrophic Lateral Sclerosis.

The SOD1-G93A transgene was designed with a mutant human SOD1 gene (harboring a single amino acid substitution of glycine to alanine at codon 93) driven by its endogenous human SOD1 promoter. This transgene was injected into fertilized B6SJLF1 mouse eggs and founder animals were obtained. Transgenic mice on a mixed B6SJL genetic background were sent to The Jackson Laboratory (as Stock No. 002726). Upon arrival, some mice were backcrossed to C57BL/6J for at least 10 generations to generate this congenic strain (Stock No. 004435). The backcross was completed in July 2002.

2. FUS-R521C Mice

FUS-R521C mice (ALS model; transgene injected into B6SJL oocytes. Maintained on C57BL/6, therefore subsequent generations have a higher percentage of C57BL/6) were selected for methods examining the effects of the addition of acetylcysteine.

Control/Non-Carrier

B6SJLF1/J (https://www.jax.org/strain/100012). Produced by a cross between a C57BL/6J (B6) female x an SJL/J (SJL) male. B6SJLF1/J mice are heterozygous for B6 and SJL alleles at all loci in their genome. This strain is often used in the production of transgenic mice.

Treatment

EH301 [Nicotinamide riboside (NR) and pterostilbene (PT)] was administered orally: 185 mg of nicotinamide riboside and 30 mg of pterostilbene/Kg×day (Estrela J M, De La Rubia J E, Dellinger R W. Treating and preventing motor neuron disease using nicotinamide riboside. PCT/US 18/32932, 2018).

Dexamethasone (DXM) was administered i.p. following sequential 4 weeks-cycle along the experimental time: 1 mg/Kg×day ($1^{st}$ week), 0.5 mg/Kg×day ($2^{nd}$ week), 0.25 mg/Kg×day ($3^{rd}$ week), 0.0 mg/Kg×day (41 week). The dose of 1 mg/Kg was selected based on Kurkowska-Jastrzebska I, Litwin T, Joniec I, Ciesielska A, Przybyłkowski A, Członkowski A, Członkowska A. Dexamethasone protects against dopaminergic neurons damage in a mouse model of Parkinson's disease. Int Immunopharmacol. 2004 October; 4(10-11):1307-18. The cyclic dose regime was designed to optimize the therapeutic benefit causing minimal possible side effects.

Ibudilast (IB) was administered orally: 12 mg/Kg×day (Wang H, Mei Zl, Zhong K L, Hu M, Long Y, Miao M X, Li N, Yan T H, Hong H. Pretreatment with antiasthmatic drug ibudilast ameliorates Aβ 1-42-induced memory impairment and neurotoxicity in mice. Pharmacol Biochem Behav. 2014 September; 124:373-9).

Acetylcysteine (NAC) was administered intraperitoneally (IP): 100 mg/kg per day, beginning on week 30, in experiments examining the effect of the addition of NAC.

Daily doses of NR, DXM and IB were administered together dissolved in 75 uL of physiological saline. PT was present in the chow of laboratory animals. The PT dose was adjusted based on the animal weight and the amount of food ingested per day.

TABLE 1

Survival time.
Kaplan-Meier curves comparing survival time between groups of mice.

| | | SOD1 | | | | | | |
|---|---|---|---|---|---|---|---|---|
| WEEK | WT | Control | EH301 | DXM | IBU | EH301 + DXM | EH301 + IBU | DXM + IBU |
| 10 | 10 | 10 | 10 | 10 | 10 | 10 | 10 | 10 |
| 11 | 10 | 10 | 10 | 10 | 10 | 10 | 10 | 10 |
| 12 | 10 | 10 | 10 | 9 | 10 | 10 | 10 | 10 |
| 13 | 10 | 10 | 10 | 9 | 10 | 10 | 10 | 10 |
| 14 | 10 | 10 | 10 | 9 | 10 | 10 | 10 | 10 |
| 15 | 10 | 10 | 10 | 9 | 10 | 10 | 10 | 20 |
| 16 | 10 | 10 | 10 | 9 | 10 | 10 | 10 | 10 |
| 17 | 10 | 8 | 10 | 9 | 10 | 10 | 10 | 10 |
| 18 | 10 | 7 | 10 | 9 | 10 | 10 | 10 | 9 |
| 19 | 10 | 5 | 10 | 9 | 8 | 10 | 10 | 9 |
| 20 | 10 | 3 | 9 | 7 | 4 | 10 | 10 | 7 |
| 21 | 10 | 0 | 8 | 4 | 3 | 7 | 10 | 5 |
| 22 | 10 | | 6 | 1 | 1 | 3 | 10 | 2 |
| 23 | 10 | | 5 | 0 | 0 | 2 | 9 | 0 |
| 24 | 10 | | 0 | | | 1 | 9 | |
| 25 | 10 | | | | | 0 | 8 | |
| 26 | 10 | | | | | | 7 | |
| 27 | 10 | | | | | | 6 | |
| 28 | 10 | | | | | | 5 | |
| 29 | 10 | | | | | | 3 | |
| 30 | 10 | | | | | | 3 | |
| 31 | 10 | | | | | | 2 | |
| 32 | 10 | | | | | | 1 | |
| 33 | 10 | | | | | | 0 | |

TABLE 2

Neurological score.

| | | SOD1 | | | |
|---|---|---|---|---|---|
| Week | WT | Control | EH301 | DXM | IBU |
| 10 | 0 ± 0 | 0 ± 0 | 0 ± 0 | 0 ± 0 | 0 ± 0 |
| 11 | 0 ± 0 | 0 ± 0 | 0 ± 0 | 0 ± 0 | 0 ± 0 |
| 12 | 0 ± 0 | 0 ± 0 | 0 ± 0 | 0 ± 0 | 0 ± 0 |
| 13 | 0 ± 0 | 0.60 ± 0.30** | 0 ± $0^{++}$ | 0 ± $0^{++}$ | 0 ± $0^{++}$ |
| 14 | 0 ± 0 | 1 ± 0** | 0 ± $0^{++}$ | 0.50 ± 0.25**$^{++}$ | 0 ± $0^{++}$ |

TABLE 2-continued

Neurological score.

| | | | | | |
|---|---|---|---|---|---|
| 15 | 0 ± 0 | 1 ± 0** | 0 ± 0$^{++}$ | 0.70 ± 0.30** | 0.30 ± 0.20**$^{++}$ |
| 16 | 0 ± 0 | 1.25 ± 0.50** | 0.50 ± 0.20**$^{+}$ | 1 ± 0** | 0.75 ± 0.60** |
| 17 | 0 ± 0 | 1.70 ± 0.45** | 0.75 ± 0.30**$^{+}$ | 1 ± 0**$^{++}$ | 1 ± 0**$^{++}$ |
| 18 | 0 ± 0 | 2.50 ± 0.60** | 1 ± 0**$^{++}$ | 1.60 ± 0.40**$^{+}$ | 1.50 ± 0.40**$^{+}$ |
| 19 | 0 ± 0 | 2.75 ± 0.50** | 1.70 ± 0.40** | 2.50 ± 0.50** | 2.20 ± 0.65** |
| 20 | 0 ± 0 | 4 ± 0** | 2.20 ± 0.50**$^{++}$ | 3 ± 0**$^{++}$ | 3 ± 0**$^{++}$ |
| 21 | 0 ± 0 | | 3 ± 0** | 3.40 ± 0.50** | 3.70 ± 0.50** |
| 22 | 0 ± 0 | | 3.50 ± 0.50** | 4 ± 0** | 4 ± 0** |
| 23 | 0 ± 0 | | 4 ± 0** | | |
| 24 | 0 ± 0 | | | | |
| 25 | 0 ± 0 | | | | |
| 26 | 0 ± 0 | | | | |
| 27 | 0 ± 0 | | | | |
| 28 | 0 ± 0 | | | | |
| 29 | 0 ± 0 | | | | |
| 30 | 0 ± 0 | | | | |
| 31 | 0 ± 0 | | | | |
| 32 | 0 ± 0 | | | | |

| | SOD1 | | |
|---|---|---|---|
| Week | EH301 + DXM | EH301 + IBU | DXM + IBU |
| 10 | 0 ± 0 | 0 ± 0 | 0 ± 0 |
| 11 | 0 ± 0 | 0 ± 0 | 0 ± 0 |
| 12 | 0 ± 0 | 0 ± 0 | 0 ± 0 |
| 13 | 0 ± 0$^{++}$ | 0 ± 0 | 0 ± 0++ |
| 14 | 0 ± 0$^{++bb}$ | 0 ± 0$^{bb}$ | 0 ± 0++ |
| 15 | 0 ± 0$^{++bbcc}$ | 0 ± 0$^{bbcc}$ | 0 ± 0++ |
| 16 | 0 ± 0$^{++aabbcc}$ | 0 ± 0$^{aabbcc}$ | 0 ± 0++ |
| 17 | 0.35 ± 0.20**$^{++bbcc}$ | 0 ± 0$^{aabbcc}$ | 0.70 ± 0.60**$^{+}$ |
| 18 | 0.80 ± 0.45** | 0 ± 0$^{aabbcc}$ | 1.20 ± 0.55**$^{++}$ |
| 19 | 1 ± 0**$^{++bbcc}$ | 0 ± 0$^{aabbcc}$ | 2.40 ± 0.70** |
| 20 | 1.50 ± 0.40**$^{++bbcc}$ | 0 ± 0$^{aabbcc}$ | 2.80 ± 0.60**$^{++}$ |
| 21 | 2.60 ± 0.75** | 0 ± 0$^{aabbcc}$ | 3 ± 0** |
| 22 | 3 ± 0**$^{bbcc}$ | 0.45 ± 0.15**$^{++aabbcc}$ | 4 ± 0** |
| 23 | 3.50 ± 0.50** | 0.70 ± 0.40**$^{++aa}$ | |
| 24 | 4 ± 0** | 1 ± 0** | |
| 25 | | 1.25 ± 0.60** | |
| 26 | | 1.74 ± 0.38** | |
| 27 | | 2 ± 0** | |
| 28 | | 2.45 ± 0.75** | |
| 29 | | 2.70 ± 0.50** | |
| 30 | | 3 ± 0** | |
| 31 | | 3 ± 0** | |
| 32 | | 4 ± 0** | |

This neurological score is based on the scale of Weydt et al. (Weydt, P., Hong, S. Y., Kliot, M., Moller, T., 2003. Assessing disease onset and progression in the SOD1 mouse model of ALS. NeuroReport 14, 1051-1054). The scores from "0" to "5" are defined as follow: "0" indicates a healthy mouse with no classical signs of ALS; "1" indicates the presence of tremors in the hind legs that occur in early disease stage; "2" indicates that mice have difficulty in separating their hind legs when suspended by their tails, which is indicative of muscle weakness; "3" is given when mice exhibit difficulty walking, either stumbling or wobbling; "4" is given when mice were unable to walk on all four legs and drag their hind legs; "5" is given when mice were unable to right themselves after 30 seconds. When the animals reach a score of "4", the access to food and water will be facilitated by placing food pellets on the cage floor to all transgenic mice. Reaching a score of "5", the animals will be euthanized for ethical reasons. Onset is defined as the earliest time when the mice show symptoms (score <4). Changes over time in the different groups were monitored weekly. The number of animals tested per week was identical to that displayed in Table 1 for each group.

TABLE 3

Rotarod test.

| | | SOD1 | | | |
|---|---|---|---|---|---|
| Week | WT | Control | EH301 | DXM | IBU |
| 10 | 1200 ± 0 | 1200 ± 0 | 1200 ± 0 | 1200 ± 0 | 1200 ± 0 |
| 11 | 1200 ± 0 | 1114 ± 59* | 1200 ± 0$^{++}$ | 1200 ± 0$^{++}$ | 1200 ± 0$^{++}$ |
| 12 | 1200 ± 0 | 1010 ± 110** | 1200 ± 0$^{++}$ | 1200 ± 0$^{++}$ | 1200 ± 0$^{++}$ |
| 13 | 1200 ± 0 | 955 ± 131** | 1200 ± 0$^{++}$ | 1200 ± 0$^{++}$ | 1200 ± 0$^{++}$ |
| 14 | 1200 ± 0 | 860 ± 114** | 1200 ± 0$^{++}$ | 1200 ± 0$^{++}$ | 1200 ± 0$^{++}$ |
| 15 | 1200 ± 0 | 720 ± 94** | 200 ± 0$^{++}$ | 1130 ± 70**$^{+}$ | 1200 ± 0$^{++}$ |

TABLE 3-continued

Rotarod test.

| | | | | | |
|---|---|---|---|---|---|
| 16 | 1200 ± 0 | 580 ± 120** | 1200 ± 0$^{++}$ | 1045 ± 166$^{*++}$ | 1200 ± 0$^{++}$ |
| 17 | 1200 ± 0 | 317 ± 77** | 1033 ± 126$^{**++}$ | 820 ± 164$^{**++}$ | 926 ± 106$^{**++}$ |
| 18 | 1200 ± 0 | 145 ± 68** | 860 ± 177$^{**++}$ | 336 ± 107$^{**+}$ | 544 ± 132$^{**++}$ |
| 19 | 1200 ± 0 | 20 ± 10** | 596 ± 144$^{**++}$ | 225 ± 80$^{**++}$ | 197 ± 101$^{**++}$ |
| 20 | 1200 ± 0 | 0 ± 0** | 233 ± 105$^{**++}$ | 161 ± 74$^{**++}$ | 102 ± 47$^{**++}$ |
| 21 | 1200 ± 0 | | 126 ± 76** | 52 ± 25** | 30 ± 16** |
| 22 | 1200 ± 0 | | 44 ± 23** | 0 ± 0** | 0 ± 0** |
| 23 | 1200 ± 0 | | 16 ± 7** | | |
| 24 | 1200 ± 0 | | | | |
| 25 | 1200 ± 0 | | | | |
| 26 | 1200 ± 0 | | | | |
| 27 | 1200 ± 0 | | | | |
| 28 | 1200 ± 0 | | | | |
| 29 | 1200 ± 0 | | | | |
| 30 | 1200 ± 0 | | | | |
| 31 | 1200 ± 0 | | | | |
| 32 | 1200 ± 0 | | | | |

| | SOD1 | | |
|---|---|---|---|
| Week | EH301 + DXM | EH301 + IBU | DXM + IBU |
| 10 | 1200 ± 0 | 1200 ± 0 | 1200 ± 0 |
| 11 | 1200 ± 0$^{++}$ | 1200 ± 0$^{++}$ | 1200 ± 0$^{++}$ |
| 12 | 1200 ± 0$^{++}$ | 1200 ± 0$^{++}$ | 1200 ± 0$^{++}$ |
| 13 | 1200 ± 0$^{++}$ | 1200 ± 0$^{++}$ | 1200 ± 0$^{++}$ |
| 14 | 1200 ± 0$^{++}$ | 1200 ± 0$^{++}$ | 1200 ± 0$^{++}$ |
| 15 | 1200 ± 0$^{++b}$ | 1200 ± 0$^{++b}$ | 1200 ± 0$^{++}$ |
| 16 | 1200 ± 0$^{++bb}$ | 1200 ± 0$^{++bb}$ | 1200 ± 0$^{++}$ |
| 17 | 1170 ± 61$^{++bb}$ | 1200 ± 0$^{++aabbcc}$ | 1200 ± 0$^{++}$ |
| 18 | 1014 ± 127$^{**++bbcc}$ | 1200 ± 0$^{++aabbcc}$ | 914 ± 117$^{**++}$ |
| 19 | 780 ± 149 $^{**++ bbcc}$ | 1200 ± 0$^{++aabbcc}$ | 328 ± 184$^{**++}$ |
| 20 | 260 ± 113$^{**++bbc}$ | 1200 ± 0$^{++aabbcc}$ | 184 ± 71$^{**++}$ |
| 21 | 110 ± 61$^{**bcc}$ | 1200 ± 0$^{aabbcc}$ | 67 ± 39** |
| 22 | 32 ± 18$^{**bbcc}$ | 1040 ± 66$^{**aabbcc}$ | 12 ± 7** |
| 23 | 0 ± 0$^{**aa}$ | 860 ± 93$^{**aa}$ | |
| 24 | 0 ± 0** | 714 ± 155** | |
| 25 | | 502 ± 160** | |
| 26 | | 320 ± 177** | |
| 27 | | 210 ± 84** | |
| 28 | | 96 ± 55** | |
| 29 | | 55 ± 23** | |
| 30 | | 25 ± 14** | |
| 31 | | 7 ± 4** | |
| 32 | | 0 ± 0** | |

Functions of the test include evaluating balance, grip strength and motor coordination of the subjects; especially in testing the effect of experimental drugs. For this test (Rota Rod, Harvard Apparatus, Holliston, MA) each animal was given three trials and the maximum period (seconds) that it could remain on a rotating axle (3.5 cm diameter; speed of rotation: 15 rpm) without falling was measured. Each mouse was given up to three attempts for an arbitrary limit of 1200 seconds and the longest period was recorded. Changes over time in the different groups were monitored weekly. The number of animals tested per week was identical to that displayed in Table 1 for each group.

Figure 3A:
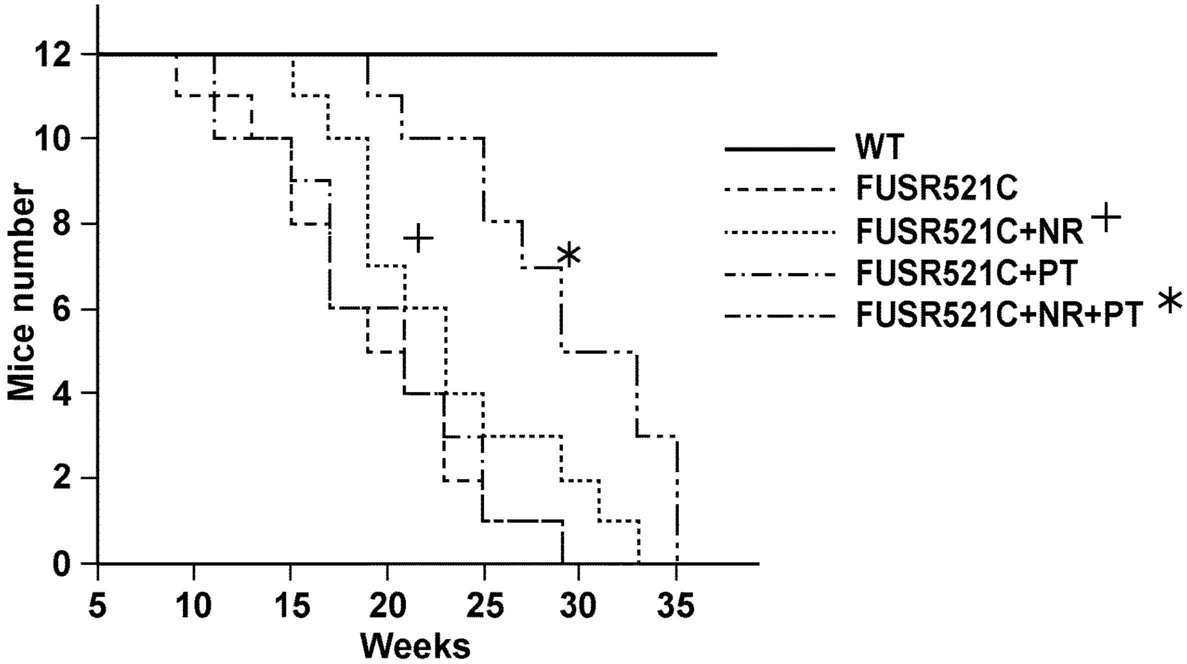
FIGS. 3A-3C illustrate survival of FUS R521C mice treated with Nicotinamide riboside (NR), pterostilbene (PT), ibudilast and N-acetyl-cysteine (NAC).
Figure 3B:
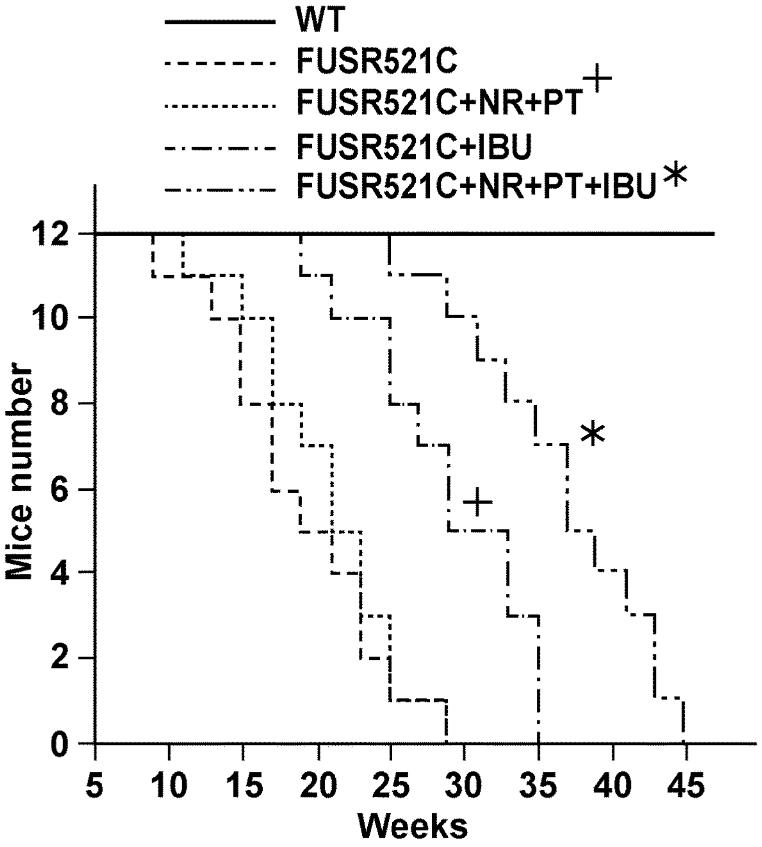
Figure 3C:
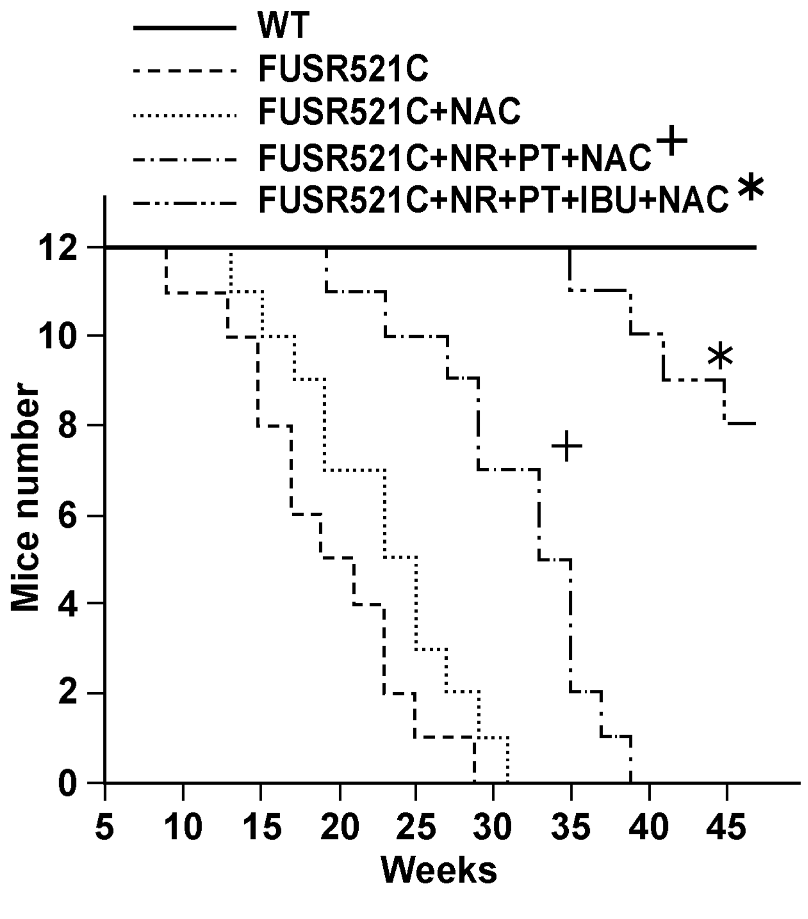

Survival of FUS-R521C mice treated with nicotinamide riboside (NR), pterostilbene (PT), ibudilast (IBU) and N-acetyl-cysteine (NAC) are illustrated in FIGS. 3A-3C. As shown in FIG. 3A, treatment with a combination of NR and PT extend survival to approximately 35 weeks, with either drug alone extending survival to about 28-32 weeks. In FIG. 3B, the combination of NR, PT and ibudilast extends survival out to approximately 45 weeks, with ibudilast alone demonstrating survival of about 30 weeks. In FIG. 3C, the combination of NR, PT, ibudilast and n-acetyl cysteine (NAC) illustrates survival beyond 45 weeks (end of study), with approximately ⅔ of the mice surviving for the entire study duration. The combination of NR, PT and NAC demonstrated survival of approximately 39-40 days, and NAC alone survival of about 32 days. These results are surprising and unexpected, illustrating that the combination of NR, PT, IBU and NAC dramatically extend the survival of the mouse model, significantly beyond any other combination and any other single compound.

Statistics

Data are presented as mean values f SD for the number of different experiments.

Statistical analyses were performed using Student's t-test.

P<0.05 and **P<0.01 comparing all SOD1 groups versus WT (wild type).

$^{+}$P<0.05 and $^{++}$P<0.01 comparing all SOD1 groups treated with EH301, DXM, IB or their combinations versus SOD1 untreated controls.

$^{a}$P<0.05 and $^{aa}$P<0.01 comparing SOD1+EH301+DXM or SOD1+EH301+IB groups versus SOD1+EH301.

$^{b}$P<0.05 and $^{bb}$P<0.01 comparing SOD1+EH301+DXM or SOD1+EH301+IB groups versus SOD1+DXM $^{c}$P<0.05 and $^{cc}$P<0.01 comparing SOD1+EH301+DXM or SOD1+EH301+IB groups versus SOD1+IB

CONCLUSIONS

The results presented herein confirm the observations presented in PCT/US 18/32932, showing that EH301 significantly increases SOD1 mice survival and improves motor-neuron dependent functions. On the other hand, administration of DXM or IB shows some improvement in both survival and motor coordination as compared to control untreated SOD1-G93A mice. Treatment with EH301 renders better results than DXM or IB.

Results using the combination of EH301 and DXM were not significantly different as compared to EH301 alone. However, remarkably, and as shown in the present examples, results using the combination of EH301 and IB were significantly better that EH301 alone.

As illustrated in FIG. 1, a significant improvement in survival was observed in SOD1-G93A mice treated from day 50 with EH301 plus Ibudilast (mean survival=191 days), relative to mice treated with either EH301 (mean survival=153 days) or Ibudilast (mean survival=137 days) ($P<0.01$).

It should be highlighted that the results presented herein clearly suggest a synergistic effect of EH301 and IB, highly superior to any other option, either currently administered to patients or being tested experimentally. Taking into account the special features of ALS (no cure, no effective treatment, nor even a way to stop or significantly slow down its fatal progression), the association of EH301 and IB may represent and encouraging new and effective therapy for the treatment of this disease.

Treatment with PDE Inhibitors

EH301 [Nicotinamide riboside (NR) and pterostilbene (PT)] is administered orally: 185 mg of nicotinamide riboside and 30 mg of pterostilbene/Kg×day.

PDE inhibitors (including PDE1, PDE2, PDE3, PDE4, PDE5, PDE 7, PDE9, PDE10, or PDE11 inhibitors) are administered orally or ip (depending on type of compound) at amounts ranging from about 1 mg to 50 mg/Kg×day.

Daily doses of NR and the PDE inhibitor are administered together dissolved in physiological saline. PT ia present in the chow of laboratory animals. The PT dose is adjusted based on the animal weight and the amount of food ingested per day.

Other experiments are designed to examine the administration of NR and PT in a single composition, along with a separate administration of PDE inhibitor. In additional experiments, NR, PT and PDE inhibitor can be included in the same composition and administered together at the same time.

In embodiments where NR and PT are administered in a single composition, a composition comprising a combination of nicotinamide riboside at 200 mg to about 700 mg and pterostilbene at about 25 mg to about 200 mg is administered to the patient, including a composition comprising amount 500 mg of nicotinamide riboside and about 100 mg pterostilbene.

In other embodiments, a composition including a combination of nicotinamide riboside at about 250 mg and pterostilbene at about 50 mg is administered to the patient. In additional embodiments, two or more doses of such as composition can be administered, such that a total of about 500 mg nicotinamide riboside and about 100 mg pterostilbene is administered to the patient on a daily basis.

PDE inhibitors, including PDE1, PDE2, PDE3, PDE4, PDE5, PDE 7, PDE9, PDE10, or PDE11 inhibitors, are administered orally or ip (depending on type of compound) at amounts ranging from about 1 mg to 50 mg/Kg×day.

Levels of proinflammatory cytokines in the cerebrospinal fluid of healthy volunteers and ALS patients has been determined as a result of treatment with EH301 alone and EH301 in combination with ibudilast. At the beginning of the procedure, the mean age of healthy volunteers and ALS patients was 51.7±3.6 years and 55.4±4.8 years, respectively. Sex distribution (males/females) in healthy volunteers and ALS patients was 8/4 (healthy volunteers), 6/4 (control ALS patients treated with placebo), 5/2 (ALS patients treated with EH301), 4/3 (ALS patients treated with EH301 and ibudilast). ALS patients were randomly distributed among the different groups. All ALS patients had a lumbar onset. At the beginning of the procedure, the duration of symptoms in the ALS patients was 15-24 months. The ALSFRS-R (revised ALS functional rating scale) score was 30-40 in all cases at the beginning of the procedure. CSF samples were taken before starting the treatment (month 0) and at 6 months.

Data represented below in Table 4 are mean values f SD for the number of volunteers or patients. Data were analyzed by two-way analysis of variance (ANOVA) (SPSS 9.0 software for Windows; SPSS Inc., Chicago, IL). The homogeneity of the variances was analyzed by the Levene test. The null hypothesis was accepted for all the values of the tests in which the F-value was nonsignificant at $P>0.05$. The data for which the F-value was significant was examined by Tukey's test at $P<0.05$. Different letters within a line indicate differences, $P<0.05$ (a>b>c).

TABLE 4

Levels of proinflammatory cytokines in the cerebrospinal fluid of healthy volunteers and ALS patients.

| | | | ALS Patients | | | | | |
|---|---|---|---|---|---|---|---|---|
| Cytokines | Healthy Volunteers | | Control | | EH301 | | EH301 + Ibudilast | |
| (pg/mL) | 0 Months | 6 Months | 0 Months | 6 Months | 0 Months | 6 Months | 0 Months | 6 Months |
| TNFα | 1.7 ± 1.4c | 1.9 ± 1.9c | 14 ± 6a | 19 ± 7a | 14 ± 9a | 12 ± 7a | 15 ± 6a | 7 ± 3b |
| IFNγ | 0.17 ± 0.16b | 0.15 ± 0.17b | 7 ± 4a | 5 ± 3a | 7 ± 4a | 4 ± 3a | 7 ± 5a | 2.7 ± 1.5ab |
| IL1β | 0.8 ± 0.6a | 0.7 ± 0.4ab | 2 ± 2a | 3 ± 2a | 1.9 ± 1.6a | 1.5 ± 0.8a | 2 ± 2a | 0.6 ± 0.2b |
| IL2 | 0.6 ± 0.6c | 0.5 ± 0.6c | 16 ± 7a | 8 ± 7a | 15 ± 6a | 10 ± 6a | 12 ± 8a | 5 ± 3b |
| IL6 | 3.0 ± 1.8a | 2.8 ± 1.9a | 4 ± 3a | 1.2 ± 1.2a | 2.1 ± 1.8a | 1.8 ± 1.3a | 1.4 ± 1.0a | 0.5 ± 0.3b |
| GM-CSF | 0.2 ± 0.3c | 0.3 ± 0.5c | 7 ± 5a | 3 ± 3a | 4 ± 4a | 4 ± 3a | 4 ± 2a | 1.5 ± 1.4ab |

This data demonstrates that the combination of EH301 and ibudilast are effective against neuroinflammation.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of treating amyotrophic lateral sclerosis (ALS) in a subject in need thereof, comprising administering to said subject a synergistic and therapeutically-effective amount of nicotinamide riboside, pterostilbene, and ibudilast, wherein said nicotinamide riboside, pterostilbene and ibudilast are administered sequentially, simultaneously, separately, or as a co-administration.

2. The method of claim 1, wherein the therapeutic effects of the nicotinamide riboside and pterostilbene have not entirely disappeared when the ibudilast is administered.

3. The method of claim 1, wherein the method further comprises administering a fatty acid supplement to the subject.

4. The method of claim 1, wherein the synergistic and therapeutically-effective amount of the nicotinamide riboside, pterostilbene, and ibudilast are included in a pharmaceutically acceptable synergistic and composition, and wherein a the nicotinamide riboside, pterostilbene, and ibudilast in the pharmaceutically acceptable composition are formulated together with one or more pharmaceutically acceptable carriers or diluents.

5. The method of claim 1, wherein the nicotinamide riboside and pterostilbene are formulated together with one or more pharmaceutically acceptable carriers or diluents, and the ibudilast is separately formulated with one or more pharmaceutically acceptable carriers or diluents.

6. The method of claim 1, wherein the nicotinamide riboside, pterostilbene, and ibudilast are each separately formulated with one or more pharmaceutically acceptable carriers or diluents.

7. The method of claim 1, further comprising administering to said subject a thiol/cysteine donor.

8. The method of claim 7, wherein the thiol/cysteine donor is selected from the group consisting of: acetylcysteine, N-acetylcysteinamide, (R)-2-Acetamido-N-cyclohexyl-3-(methylthio) propenamide, (R)—N-Cyclohexyl-3-(methylthio)-2-propionamidopropanamide, (R)-2-Acetamido-3-(methylthio)-N-phenylpropanamide, N-acetylcysteine benzyl ester, and N-acetylcysteine ethyl ether.

* * * * *

UNITED STATES PATENT AND TRADEMARK OFFICE

CERTIFICATE OF CORRECTION

PATENT NO. : 12,350,283 B2
APPLICATION NO. : 17/432994
DATED : July 8, 2025
INVENTOR(S) : José María Estrela Arigüel et al.

It is certified that error appears in the above-identified patent and that said Letters Patent is hereby corrected as shown below:

In the Claims

Column 30, Line 7, Claim 4:
Delete the term "synergistic and".

Column 30, Line 8, Claim 4:
Delete the "a" in "wherein a the nicotinamide ribose".

Column 30, Lines 26-27, Claim 8:
Replace the compound name "(R)--N-Cyclohexyl-3-(methylthio)-2-propionamidopropanamide" with --(R)-N-Cyclohexyl-3-(methylthio)-2-propionamidopropanamide--.

Signed and Sealed this
Ninth Day of September, 2025

Coke Morgan Stewart
*Acting Director of the United States Patent and Trademark Office*